United States Patent [19]

Daly et al.

[11] 4,408,608
[45] Oct. 11, 1983

[54] IMPLANTABLE TISSUE-STIMULATING PROSTHESIS

[75] Inventors: Christopher N. Daly, Bilgola Plateau; David K. Money, Pennant Hills, both of Australia

[73] Assignee: Telectronics Pty. Ltd., Lane Cove, Australia

[21] Appl. No.: 252,319

[22] Filed: Apr. 9, 1981

[51] Int. Cl.³ .............................................. A61N 1/30
[52] U.S. Cl. .................................................. 128/421
[58] Field of Search .............. 128/419 R, 419 F, 421, 128/422, 423

[56] References Cited

U.S. PATENT DOCUMENTS

| | | | |
|---|---|---|---|
| 3,662,758 | 5/1972 | Glover | 128/419 R |
| 3,667,477 | 6/1972 | Susset et al. | 128/419 E |
| 3,727,616 | 4/1973 | Lenzkes | 128/422 |
| 4,019,518 | 4/1977 | Maurer et al. | 128/419 R |

Primary Examiner—Wm. E. Kamm
Attorney, Agent, or Firm—Gottlieb, Rackman and Reisman

[57] ABSTRACT

There is disclosed an implantable tissue-stimulating prosthesis, such as a cochlear prosthesis, which can not only be implemented in single-chip form, but which also permits great flexibility in stimulation strategy and data transmission format. Only sixteen electrodes are required for stimulating fifteen different sites. Each site is stimulated by a biphasic pulse under control of two adjacent electrodes whose polarities are reversed in the middle of the site stimulation cycle. Although the transmission scheme requires a pulse-width modulation format, the precise form of the format can be varied in order to accommodate widely different stimulation strategies. For example, only a single site may be stimulated during each transmission frame or multiple sites may be stimulated during the same frame. Although only one site can be stimulated at any instant of time, the system cycling is so fast that "simultaneous" site stimulations are perceived. The system is designed for minimum power usage, and its operation is fail-safe in that no site may be stimulated for longer than a pre-set time interval.

145 Claims, 9 Drawing Figures

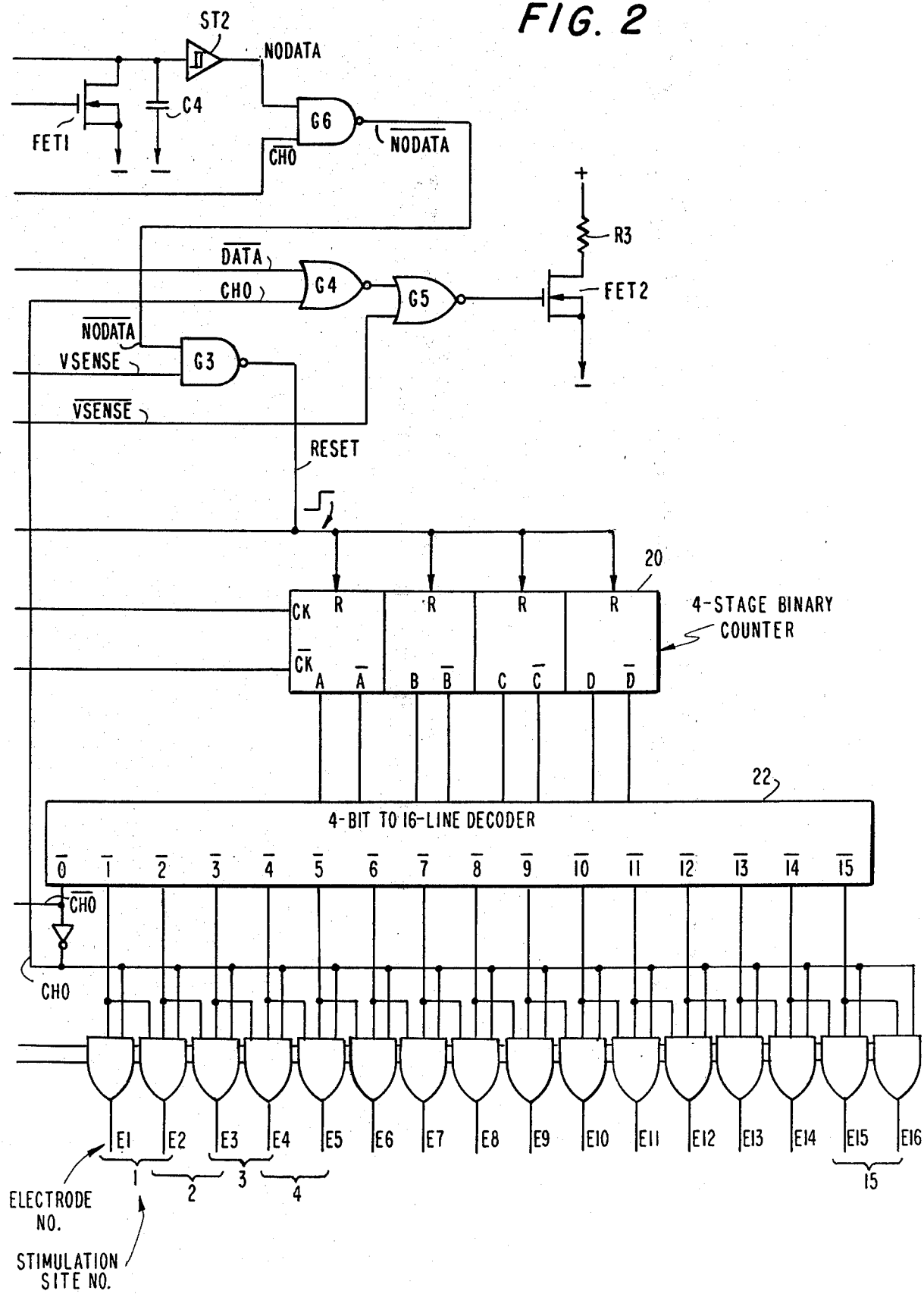

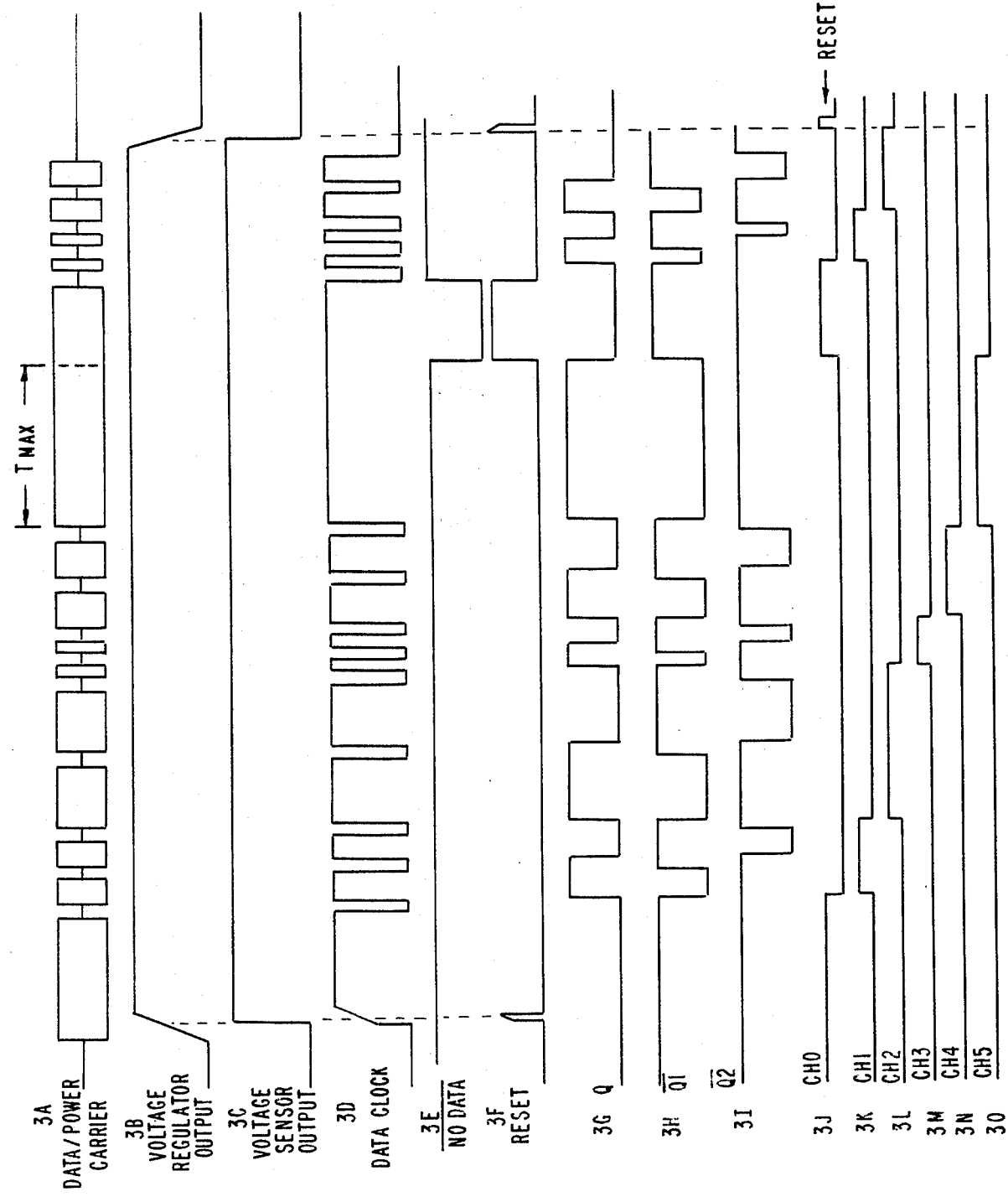

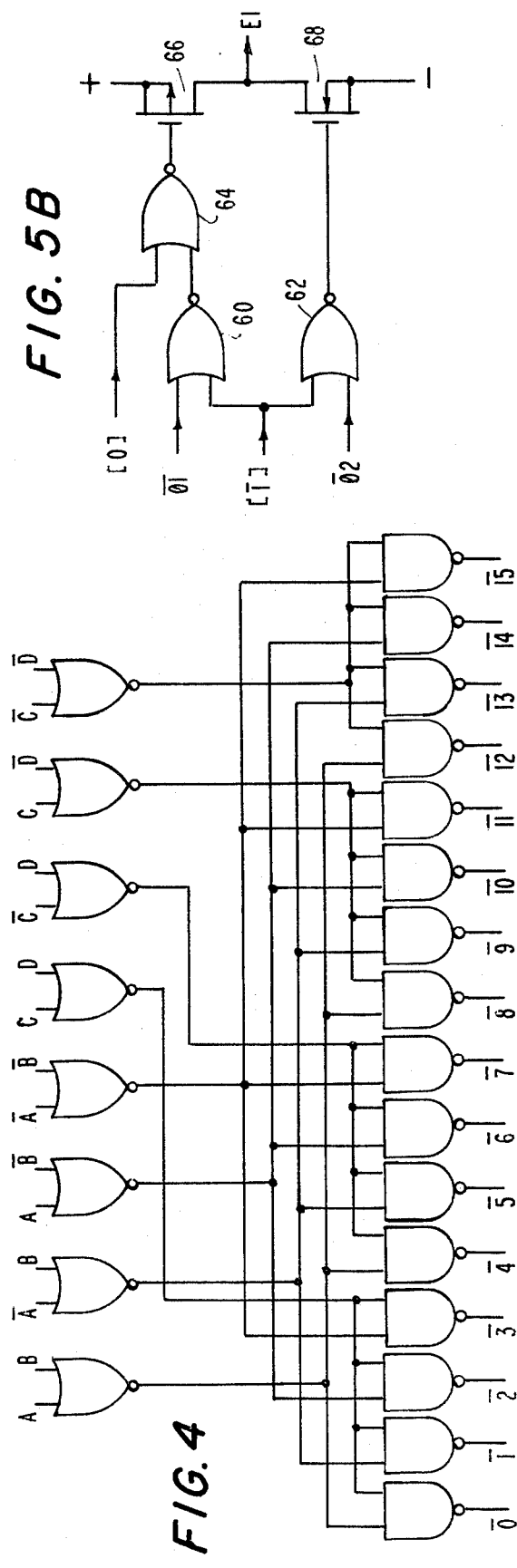
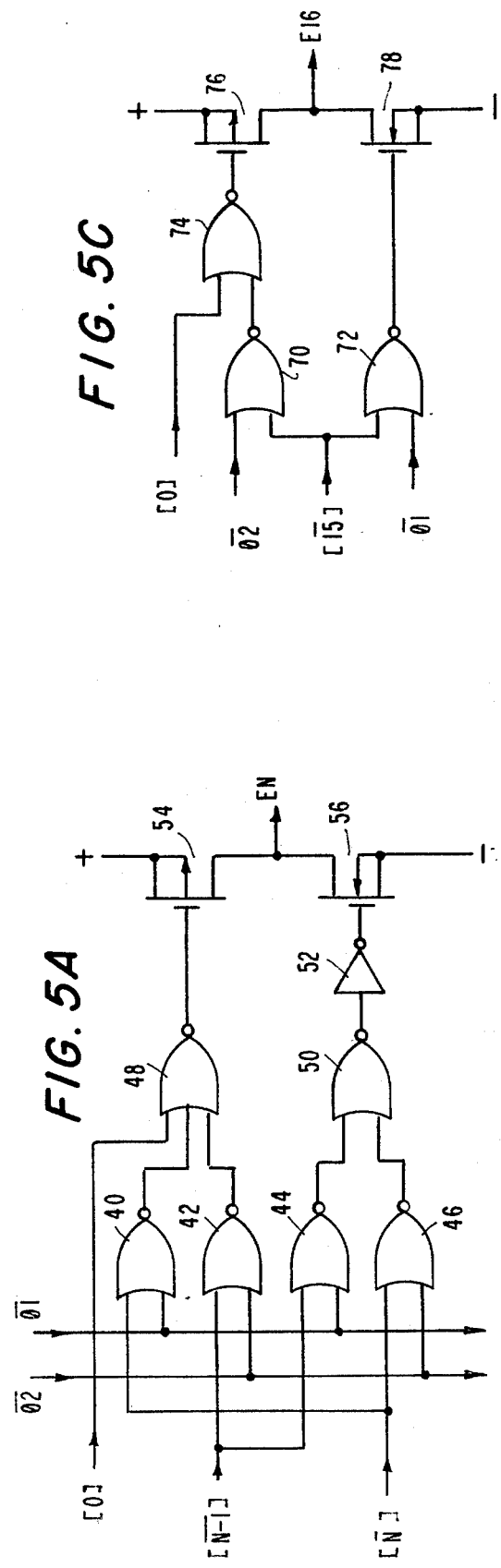

IMPLANTABLE TISSUE-STIMULATING PROSTHESIS

This invention relates to implantable tissue-stimulating prostheses, and more particular to a prosthesis which offers numerous advantages, including those of small size (single-chip implementation), reliability, and flexibility in operation.

In recent years, more and more attention has been paid to implantable prostheses, such as those used for cochlear stimulation, chronic pain relief, cerebellar stimulation, and visual stimulation. Typically, in a cochlear prosthesis, an implantable package is fitted into a surgically-created cavity within the mastoid bone behind the ear, the cavity providing access to the cochlea to facilitate electrode insertion. Because power consumption under typical stimulation conditions is too high for a power source to be contained within the package, power as well as electrical stimulation information is usually coupled transcutaneously to the implanted receiver-stimulator. Because it is necessary to transmit data to the implanted device anyway, it is not particularly difficult to transmit power as well as via inductive coupling. Some background prior art is as follows:

"A Multiple Electrode Hearing Prosthesis For Cochlear Implantation in Deaf Patients", Clark, G. M., et al, Medical Progress Through Technology, Vol. 5, No. 3, 15 Dec., 1977.

"A CMOS Implantable Multichannel Auditory Stimulator for the Deaf", Gheewala, et al, I.E.E.E. Journal of Solid State Circuits, Vol. SC10, No. 6, Dec., 1975.

U.S. Pat. No. 3,449,768, J. H. Doyle, "Artificial Sense Organ".

U.S. Pat. No. 3,752,939, M. C. Bartz, "Prosthetic Device for the Deaf".

U.S. Pat. No. 4,036,048, Kissiah, Jr., "Implantable Electronic Hearing Aid".

French Pat. No. 2,383,657, C. Ricard, P. MacLeod and C. H. Chouard, "Equipement Pour Prothèse Auditive".

Provisional Patent Specification, University of Melbourne, "Improvements in Prosthesis", Commonwealth of Australia, Ser. No. PD 2291/77.

The investigative work done thus far has given rise to certain requirements, in addition to those mentioned above, which should be met by any practical cochlear prosthesis. About 15 electrode sites must be independently stimulated in order to convey a sufficient spectrum of sounds for speech comprehension. It is almost never necessary to stimulate all sites simultaneously. In fact, current speech-processing strategies stimulate only one or two sites at any one time. Stimulations at two or more sites simultaneously results in charge addition and subtraction effects, which effects complicate the stimulation model and make it more difficult to formulate effective speech-processing strategies. Experiments have shown that there is little or no perceptual difference between stimulating a plurality of sites simultaneously, or sequentially but all within a short interval of less than one millisecond; whatever differences may exist can be compensated for in the speech processing strategy which is employed. Also, when the stimulation rate is increased beyond 300–500 Hz there is little perceptual difference, this phenomenon probably being related to the maximum firing rate of nerve fibers.

There are several parameters of electrical stimulation which can be changed to alter the perceived pitch and intensity of sound. In addition to cochlear site, i.e., which of the multiple electrode sites is energized, two of the most important parameters are pulse repetition rate and pulse energy. The site, rate and energy parameters are interdependent to a degree and can be interacted to construct different percepts. One of the difficulties in defining auditory electrical stimulation parameters is the wide range of thresholds of stimulation, and the highly compressed electrical dynamic range. Stimulation thresholds (the pulse energies required for just perceiving a sound) vary over a 30–40 dB range not only from patient to patient, but even from electrode to electrode for any one patient. At the same time, a relatively small increase in energy of only 6 dB can produce a change in perceived intensity of 60 dB, 60 dB being the range from approximately "just noticeable" to "uncomfortable" on the intensity scale. What this means is that within the entire range of stimulation energy, the particular range for any given electrode is relatively small, but it may be anywhere within an overall broad range. Because the dynamic ranges for different electrodes may be widely separated within the overall energy stimulation range, the prosthesis must be capable of very great resolution. An implantable auditory nerve stimulator must provide a wide range of pulse energies, at the same time that it is able to control a useful number of perceived intensities for any given electrode within a small range of pulse energies.

The implanted system must be intrinsically safe in that it must prevent the possibility of excessive stimulation which might otherwise damage sensitive nerve endings. It has also been determined the the output pulses should be biphasic in order to minimize electrochemical effects which would result from charge imbalance at any electrode site; at any stimulation site, there should be a first pulse, followed by a second equal pulse of the opposite polarity. Biphasic stimulation minimizes electrolytic and bio-electric effects, such as gas evolution, electrode dissolution and bone growth.

The present invention does not pertain to speech processing strategies nor to transmitter designs. Much investigative work is being done in this area. The present invention is an implantable prosthesis itself. But the prosthesis should facilitate low-power operation of the external speech processor/transmitter, that is, it should require minimum standby power and should permit efficient power and data transmission modes. These are desirable characteristics of any implantable prosthesis, no matter what the form of the external processor/transmitter.

One of the most important requirements of any cochlear prosthesis is that it be highly reliable in operation, reliability being enhanced by the system having as few components as possible and preferably comprising only one or at most two integrated circuit chips; reliability increases with a decrease in the number of chip interconnections. (Yet another advantage of system simplicity is that the package size can be kept to a minimum, especially if an output capacitor is not required for each electrode, as in our invention). Reliability is very important for a cochlear implant because it is not yet known whether the electronic package (including the electrodes) can be removed from a patient without causing irreversible damage to the cochlea. While it would be possible to interpose a connector between implanted electrodes and the electronic package, that would introduce an additional component which might fail, not to mention that connectors are notorious for their poor reliability under adverse conditions, especially those of body fluids. Once the implant is functioning and stable in the body, it becomes the patient's means for perceiving sound. The patient has to undergo considerable rehabilitation to learn to hear, and to interpret what he hears, since although ideally the device should recreate sound as people with normal hearing hear it, it can only be approximated via electrical stimulation. It is not yet known whether a second implantation after explant of a faulty device would be a viable procedure and, even were it viable, further rehabilitation might well be necessary. For these reasons, reliability is a main design objective of any implantable cochlear prosthesis.

Another important design objective is flexibility in operation. Until the most effective speech processing strategies are determined, a cochlear implant should allow variations in stimulation sequencing.

The prosthesis of our invention is designed to meet all of the above requirements. The illustrative embodiment of the invention is a 15-channel receiver/stimulator capable of providing biphasic, constant-amplitude, variable width pulses at a rate sufficient to provide maximum stimulation to at least three channels within a one-millisecond frame. (As mentioned above, this is perceived as simultaneous excitation and there is rarely a need to energize more than three sites simultaneously.) Power and data are inductively coupled on the same carrier so that only a single coil is required for receiving both power and data. (This, in and of itself, is a prior art technique; it has been recognized that a single carrier should be used if simplicity and small size are to be achieved.) The receiver is designed for intermittent operation. It need not be operated during silent periods. Also, speech contains a high degree of redundant information, and many of the speech processing strategies being investigated result in frequent non-stimulating intervals. The device is capable of rapid power-up and power-down, and always returns to a reset state when the power supply voltage drops below a pre-set threshold with cessation of carrier transmission.

One of the most important features of our invention is the electrode arrangement. There are only sixteen electrodes which are required to provide fifteen stimulation sites (or channels). Each channel has two phases. The first is the negative stimulation phase in which the selected electrode N goes negative with respect to the adjacent electrode (N+1). The second phase, the positive stimulation phase, is that in which the polarities of the same two electrodes are reversed. During the two phases for any channel, all non-selected electrodes are open-circuited. At all other times, and during "channel zero" selection (the reset condition), all electrodes are connected together. By connecting all of the electrodes together, any residual charge at the electrodes is dissipated and electrode polarization currents are minimized. The shorting together of the electrodes takes place both at the end of each frame (channel cycling) and at the start of the next frame, to ensure residual charge dissipation.

This technique of pairing electrodes has no counterpart in the prior art. One prior art technique involved the use of an electrode array with a common ground electrode external to the cochlea. This approach results in broad stimulation due to the unpredictable current paths through the cochlea. Another approach was to provide alternate electrodes connected together as a common ground. This approach does result in a more localized current flow for low charge levels, but the multiple ground connections give rise to increased current spreading at high charge levels. Also, a major disadvantage of this approach is that it requires twice as many electrodes for the same number of channels, since a ground electrode is provided for each active electrode. Perhaps the best prior art electrode array is that which includes individually switched bipolar pairs. For each site to be stimulated, a respective pair of electrodes is provided and biphasic pulses are applied to the pair. This does provide bipolar stimulation with minimal current spreading. But it requires twice as many electrodes as stimulation sites. With the switching scheme of our invention, only sixteen electrodes are required for fifteen stimulation sites, despite the fact that there is true bipolar stimulation with minimal current spreading.

The molded electrode support is typically 20 mm in length, and has a tapered diameter which varies between 0.5 and 1.5 mm, with the individual electrodes being distributed along its length. It is apparent that assembly of an electrode array can be simplified considerably if relatively few electrodes are required.

The reason that electrode switching in this way can be effective is that typically at most three channels require simultaneous stimulation, and the stimulation is perceived as being "simultaneous" if the three sites are energized sequentially in less than one millisecond. (Some investigators, notably Ricard, MacLeod and Chouard, claim that sequential energization within two milliseconds is sufficient.) Because true simultaneous energization of multiple electrode sites is thus not required, there is no need to have an independent pair of electrodes for each channel. Two adjacent channels may be energized "simultaneously" (sequentially, but fast one after the other) even though they share a common electrode.

Another advantage of sequential stimulation is that the problem of adjacent channel current summing (which would otherwise occur in the event of two adjacent bipolar pairs being energized simultaneously) is avoided. Also, only one supply voltage is required, biphasic pulses being generated between two adjacent electrodes by first switching one negative with respect to the other, and then reversing the connections. The use of two supplies would necessitate two supply storage capacitors, which would work against the requirement of small size. There is no problem with supply voltage matching with a single supply in our invention because both phases of the biphasic pulse are switched through identical P-channel and N-channel switches in series with the electrodes for the two phases.

The data for the receiver/stimulator consists of carrier bursts. Preferably, although not mandatory, a pair of equal-width bursts is provided for each channel, one burst in each pair controlling a respective phase of the biphasic pulse. The widths of the two pulses for any channel which is not to be stimulated are short enough such that while an internal counter is advanced, stimulation is not perceived. Thus to select a specific stimulation site after power-up, the first $N-1$ sites are sequentially selected at the maximum scan rate which allows the internal channel selection counter to count, while no effective stimulation is actually provided to the electrodes. After the required $2(N-1)$ short carrier bursts, the next two bursts represent the first and second phases for channel N, with the widths of the two bursts each being in the range 1–100 microseconds. This form of pulse width modulation allows maximum resolution; the analog technique is in this case better than a digital technique.

The time required to cycle through a channel without stimulating the respective site may be six microseconds per phase (with the carrier being on for four microseconds, and off for two microseconds). Thus 12 microseconds are required to "skip over" any channel, and 180 microseconds would be required to skip over all fifteen channels. Such a high speed permits several different options for stimulating the electrodes. For example, suppose that 3 sites are to be maximally stimulated in one frame, and no attention is even paid to ending the frame after the last site is stimulated (e.g., cycling is through all 15 channels even though the third and last channel requiring stimulation may be channel number 7). Skipping over 12 channels requires (12) (12) or 144 microseconds, and stimulation of 3 channels requires 600 microseconds. If the power-up and power-down times for the frame are each 50 microseconds, even such a timewise inefficient scheme requires a frame length of only 844 microseconds—short enough to allow the 3 selected sites to be stimulated "simultaneously". When implemented in an integrated circuit, even fewer than 12 microseconds would be required to skip over a channel due to the increased speeds which would be possible.

Interestingly, the stimulation threshold with very short pulses actually increases when the two phases of a pulse are very close together. During cycling and skipping over of unselected channels, the two phases are separated by only two microseconds. This further insures that the short pulses for any channel to be skipped over do not result in perceptible stimulation because the stimulation threshold is higher than usual when the two pulses in any pair are close together.

Whether only one or several sites are effectively stimulated during each frame, carrier transmission may cease (or the system otherwise reset) immediately after the last site to be stimulated is acted upon, rather than continuing to cycle all the way through the last channel. This would allow another frame to begin immediately if one is needed. As will be described below, when carrier transmission ceases the system automatically resets and idles in channel 0—at which time no sites are stimulated and instead all of the electrodes are shorted together—until the stored energy has dissipated, if it dissipates before the start of transmission of a new information frame. This scheme allows great flexibility in that the stimulation strategy can be wholly determined by the external processor. The implanted device permits many different stimulation formats, i.e., full or partial 15-channel frames, and single or multiple site stimulations per frame.

As important as carrier termination is its nonstop transmission. Continuous carrier transmission without data breaks is interpreted as a reset signal; if there is a fault in the transmission system, it is in this way not possible to apply a continuous excessive current to an electrode. Continuous carrier detection results in channel 0 being selected and the shorting of all electrodes.

The system is provided with added flexibility because the separation between pulses in any pair is simply a function of the width of the carrier break. It is just as easy to adjust the delay between phases as it is to adjust phase width. This would not be the case were the biphasic pulse generator solely controlled within the prosthesis itself. Once again, it is envisioned that as time goes by, much will be learned about more effective stimulation strategies. One of our design objectives was to provide a prosthesis which might work with all such strategies, even those which take into account pulse separation as a stimulation parameter. Thus, patients implanted with the device of our invention will be able to benefit from future improved speech processing strategies without any need to replace or modify the device itself.

The conventional state-of-the-art approach to designing a multi-channel stimulation device (without taking into account the specific natures of stimulation strategies) is to encode the stimulation parameters and a relevant electrode address into a binary word, to transmit the binary data, to decode it in the receiver in order to retrieve the address and stimulation parameters, and to convert the digitally-encoded parameter values to an analog charge level and to deliver the appropriate charge to the addressed electrode. This approach has been used and it works. But it requires a considerable amount of circuitry, not only in the external system, but also in the implanted prosthesis. The number of charge levels which can be accurately delivered is dependent upon the number of bits used to encode the charge level and this, in turn, depends upon the complexity and accuracy of the D/A conversion circuitry. In the scheme of our invention, on the other hand, the theoretical resolution of pulse width is approximately 0.33 microseconds (one cycle of the 3 MHz carrier which is used) in 100 microseconds, which is the equivalent of about 300 discrete levels—despite the fact that the circuitry itself is relatively simple. Pulse width is determined solely by the external system, and there is no A/D and D/A conversion which is interposed. Resolution in energy delivery is very important because of the wide range of stimulation thresholds. For example, one electrode may have a threshold width of 10 microseconds, in which case the threshold of discomfort would be about 20 microseconds. Thus in the system of the invention 30 levels between 10 microseconds and 20 microseconds can be resolved, even though probably no more that 16 levels may actually be useful. If the threshold and discomfort levels are respectively 50 microseconds and 100 microseconds, then 150 levels can be resolved, a number which is far more than necessary. In all cases, it is a trivial matter for the external system to set the step size (resolution) for each stimulation site.

Further objects, features and advantages of our invention will become apparent upon consideration of the following detailed description in conjunction with the drawing, in which:

FIGS. 1 and 2, with FIG. 1 being placed to the left of FIG. 2, depict the illustrative embodiment of the invention;

FIG. 3 is a timing diagram which will be helpful in understanding the operation of the system of FIGS. 1 and 2;

FIG. 4 depicts the details of the 4-bit to 16-line decoder of FIG. 2;

FIGS. 5A–5C depict the details of the output stages shown in symbolic form only at the bottom of FIG. 2.

Figure 1:
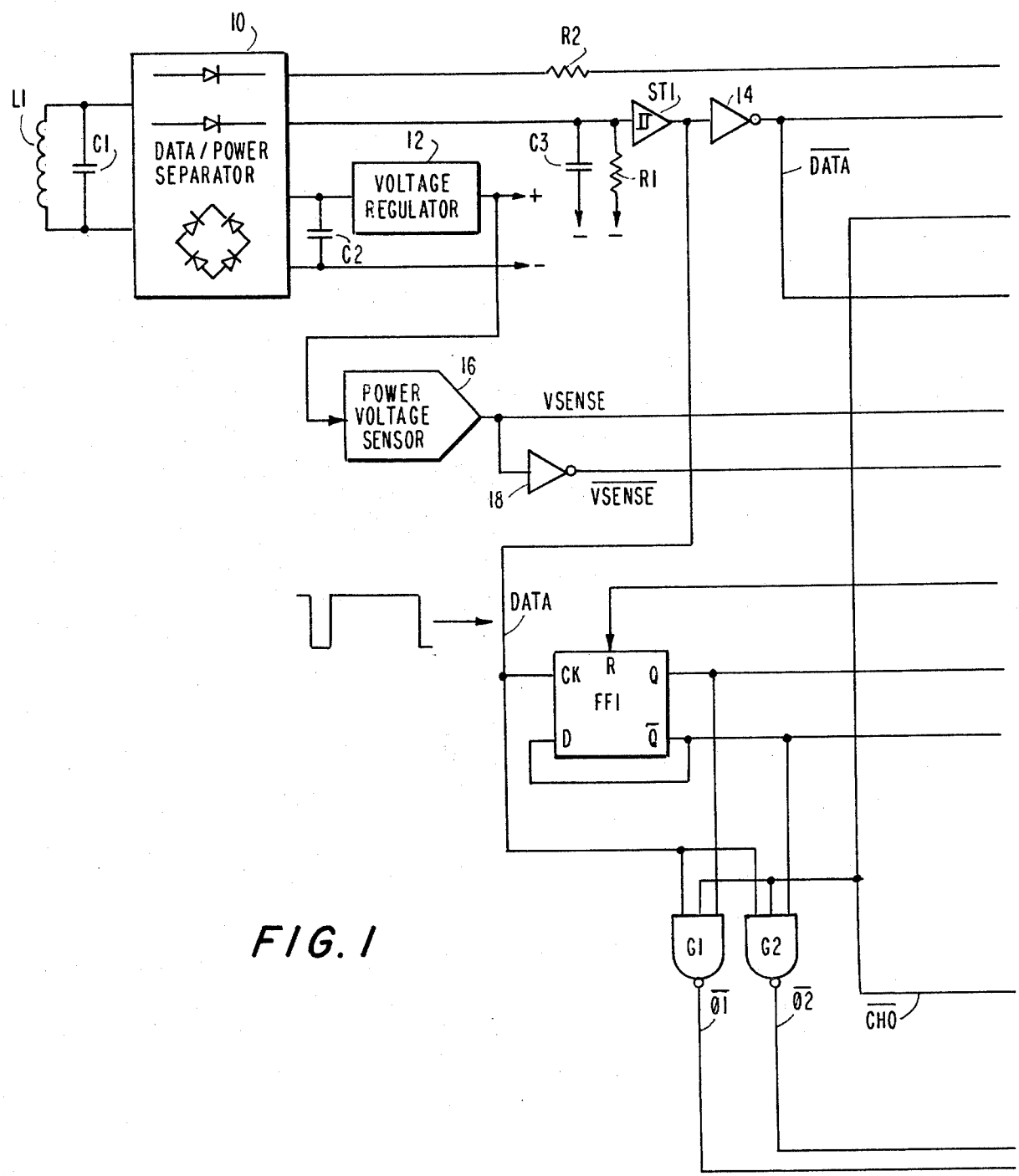

The data/power carrier consists of a train of closely spaced RF bursts. Pick-up coil L1 in FIG. 1 is tuned to the transmitter frequency by capacitor C1. In the illustrative embodiment of the invention, a carrier frequency of 3 MHz is utilized. The Q of the resonant circuit is low (about 3) in order that the tuning be non-critical, and in order to minimize the rise and fall times of the peak voltage across the resonant circuit in response to the burst mode transmission.

Data/power separator 10 may take any of prior art forms. In its simplest form, the unit consists of a full-wave bridge rectifier for powering the logic by developing a potential across capacitor C2, the capacitor serving to filter the output of the rectifier circuit. A preferred data/power separator is disclosed in our co-pending application Ser. No. 252,313, filed on even date herewith and entitled "On-Chip CMOS Bridge Circuit", which application is hereby incorporated by reference. Voltage regulator 12 derives a voltage in the range 3-4 volts for powering the system. The voltage across capacitor C2 normally varies with coil separation and circuit load, and the voltage regulator is necessary to ensure repeatable and predictable charge delivery to the electrodes. The voltage regulator itself may be of conventional design, e.g., shunt or series.

Two half-wave rectifiers are also provided in unit 10 in order to demodulate the carrier signal and to provide direct envelope information which is fed to the two Schmitt trigger circuits ST1 and ST2. The signal delivered to Schmitt trigger ST1 is used to clock the counter as the system cycles through the 16 channels, reset channel 0 and the active channels 1–15. Resistor R1 and capacitor C3 determine the rise and fall times, and the ripple, of the signal at the input of Schmitt trigger ST1, and their values depend on the range of the pulse widths in the transmitted signal. The other half-wave rectifier in data/power separator 10 is used to charge capacitor C4 through resistor R2. The associated logic is a safety feature which prevents the system from stimulating one of the outputs in the unlikely event of the external transmitter providing a continuous RF carrier with no data breaks. This would be a problem if it occurred during a channel scanning sequence with one of the active channels being energized, or if the receiver counter (to be described below) miscounted and some channel other than channel zero was represented by the count at a time when channel zero should be represented. Under such a false condition, it would be undesirable to provide a continuous DC current to one of the electrodes. Despite the fact that the external transmitter would in almost all cases have its own safety circuit to monitor its output in order to prevent such a condition from arising, it is still desirable for the implanted device to be intrinsically fail-safe.

In the presence of an RF carrier, capacitor C4 charges through resistor R2 to the switching threshold of Schmitt trigger ST2. When the capacitor charges to the threshold level of the Schmitt trigger, its NODATA output goes high to control a reset of the counter and the selection of channel zero, as will be described below. As long as data is being transmitted, the output of Schmitt trigger ST1 follows the envelope of the carrier, the envelope (DATA signal) being shown in the drawing. Each pulse of a channel pair consists of a rising edge, followed by a falling edge. Whenever there is a break in the carrier transmission, i.e., data is being transmitted because the end of a pulse has been detected, the output of Schmitt trigger ST1 goes low, and the output of inverter 14 goes high. This causes transistor FET1 to turn on and to discharge capacitor C4. Consequently, as long as the carrier is not transmitted continuously long enough for capacitor C4 to charge to the firing level of Schmitt trigger ST2, the NODATA output of Schmitt trigger ST2 remains low; soon after capacitor C4 starts to charge at the start of a data pulse, it is discharged with the arrival of a data break, the end of the pulse, when transistor FET1 turns on. It is only if the carrier is transmitted continuously for longer than TMAX seconds (see FIG. 3) that the NODATA output goes high. Since in the illustrative embodiment of the invention the maximum data pulse width is 100 microseconds, the component values should be selected such that TMAX is slightly greater than 100 microseconds.

Although unit 10 is shown as having two half-wave rectifiers for deriving separate inputs for Schmitt triggers ST1 and ST2, it may be sufficient to provide only one rectifier. In such a case, because a fast rise time is required for capacitor C3, resistor R2 would have to be high enough to have a negligible effect on capacitor C3. But there would be no particular advantage in using only a single rectifier in an integrated circuit embodiment, especially if discrete capacitors are not required for capacitors C3 and C4, and on-chip capacitances are used instead.

The output of voltage regulator 12 is applied to power voltage sensor 16. This element detects the level of the powering potential. The VSENSE output is high whenever the output of the voltage regulator exceeds a power threshold level, the threshold level being higher than the potential actually required to power the circuit logic. Inverter 18 causes an opposite polarity signal to appear at its output, the VSENSE line.

The first three waveforms in the timing diagram of FIG. 3 depict respectively a typical data/power transmission sequence, the voltage regulator output, and the voltage sensor output. The initial carrier burst powers up the circuit. The voltage sensor output goes high before the maximum powering potential is derived, but after a potential is reached which can actually operate the logic elements.

Waveform 3D depicts the output of Schmitt trigger ST1, referred to as the data clock. Except for the initial rising edge which is not sharply defined if the stored energy has dissipated and the voltage regulator output must build up, the data clock waveform represents the demodulated carrier. Following the initial power-up portion of the transmission, the first data break (negative transition) signals that a pair of pulses is about to arrive. As seen in the waveforms 3A and 3D, each channel is represented by two equal-width pulses, and there is a two-microsecond separation not only between the two phases of each channel pair, but also between successive pairs of pulses.

Counter 20 keeps track of the channel being operated upon. Reset of the counter, to represent channel 0 (the safety feature), is controlled by the NODATA output of gate G6 going low. Whenever continuous RF has been received for longer than TMAX seconds, the NODATA line is high in potential. Assuming that the CH0 (channel 0) input of gate G6 is high, the high potential on the NODATA line causes the output of gate G6 to go low. Since the VSENSE line is high during data transmission, when the NODATA input of gate G3 goes low, the output of gate G3 (reset) goes high to reset both counter 20 and flip-flop FF1 (see waveforms 3E, 3F and 3G). The NODATA-controlled reset is inhibited if the system is in channel 0, for reasons which will become apparent below, by using the CH0 signal to hold the output of gate G6 high; the $\overline{CHO}$ line is low when the system is in channel 0.

Although counter 20 defines which of 16 channels is being operated upon, each channel has two phases. The phases are defined by flip-flop FF1. When the flip-flop is reset with its $\overline{Q}$ output high, the system is in phase 2 of a channel; when the flip-flop is set with its Q output high, the system is in phase 1 of a channel. Because the $\overline{Q}$ output of the flip-flop is fed back to its D input, successive clock (rising edge) inputs toggle the flip-flop. The Q and $\overline{Q}$ outputs are coupled to the clock inputs of the first stage of counter 20. As a result, whenever the flip-flop toggles to represent phase 1 of a channel, the counter is advanced to represent a new channel.

There are many different transmission schemes which may be employed and it is important to understand how the system resets in each case. In one general, preferred type of transmission scheme, the carrier frequency is not transmitted between information frames. This not only conserves energy, but it also prevents tissue from being exposed continuously to RF radiation when stimulation is not actually required; even during speech, there are many intervals when stimulation is not required. In those cases where the carrier is not transmitted between frames, the end of a frame is actually indicated by the VSENSE line going low, as will be described in detail below. But that does not mean that there is then insufficient charge stored on capacitor C2 for powering the logic elements. In some cases there may even be enough charge left to power the system at the start of the next frame, if it arrives before the charge on capacitor C2 has dissipated appreciably. It is important that the system be synchronized to the next information frame whether or not there is sufficient charge on capacitor C2 for powering the logic immediately at the start of the next transmission.

In such modes of operation in which carrier transmission ceases between frames, the necessary synchronization can be achieved by always providing an initial carrier burst at the start of any frame, the burst being long enough to power up the circuit even though there already may be sufficient charge on capacitor C2 for actually powering the logic. By the end of the initial power-up carrier burst, the system should be in channel 0, phase 2; this way, after the first data break, the rising edge of the information signal on the DATA line, which represents the start of the first data pulse, may toggle flip-flop FF1 to the set state (phase 1) and advance the counter from representing channel 0 to represent channel 1.

Consider the first case in which there is a sufficiently long time after the cessation of carrier transmission not only for the VSENSE line to go low to indicate the end of a frame, but also for the voltage regulator output to fall so low that the logic elements cannot be operated. It is this case which is shown in FIG. 3, with the voltage regulator output of waveform 3B going to zero soon after the voltage sensor output of waveform 3C goes low. As soon as the VSENSE output goes low at the end of the frame, gate G3 operates since it is still powered by the charge remaining on capacitor C2, and its output goes high to reset the counter to represent channel zero, and the flip-flop to represent phase 2. The counter must be reset to channel 0 so that all of the electrodes will be shorted together for charge dissipation purposes. Whether the system remains in channel zero depends upon whether the voltage regulator output falls to zero prior to start of the next frame. If it does, all synchronization information is lost since the system is not powered at all, and it is necessary to re-synchronize the system to the start of the next transmission frame. This is the case shown in FIG. 3; the reset pulse at the end of waveform 3F is shown terminating together with the falling off of the voltage regulator output.

At the start of the next frame, during the power-up carrier burst, the system is re-synchronized to channel zero, phase 2. During the initial carrier burst, the voltage regulator output builds up gradually, as depicted in waveform 3B. As it builds up, a sufficient potential is derived for powering the logic before the potential is high enough to cause the VSENSE line to go high. Consequently, after the potential builds up to a level sufficient for powering the logic and until the VSENSE line goes high, the output of gate G3 is high to reset the system in channel 0, phase 2. It is important to note that flip-flop FF1 is not clocked by the signal appearing on the DATA line. This signal builds up gradually, but as its leading edge is being formed the flip-flop is held reset by the reset pulse of waveform 3F. By the time the reset pulse terminates with the VSENSE line going high, the flip-flop cannot be effectively clocked by what is left of the rising edge of the DATA clock waveform. Consequently, the system remains reset in channel 0, phase 2 until after the first data break. On the leading edge of the next pulse—the start of the first data pulse—the flip-flop is clocked so that it represents phase 1, with counter 20 being advanced to represent channel 1. Thus the system is placed in channel 1, phase 1 at the start of the first data pulse and necessary synchronization has been achieved.

On the other hand, suppose that the time between frames is not sufficient for the voltage regulator output to completely die down. That is, although the VSENSE line goes low to indicate the end of a frame, sufficient charge is maintained on capacitor C2 between frames to power the logic. In this case, because the VSENSE line is low, the reset output of gate G3 will remain high. Instead of there being a short pulse as shown at the end of waveform 3F, the RESET line remains high, and the counter and the flip-flop are held reset in channel 0, phase 2. At the start of the next frame, with transmission of the power-up carrier burst, the DATA clock signal of waveform 3D has a sharply defined rising edge which would otherwise clock the flip-flop, since the logic is still being powered and Schmitt trigger ST1 follows the incoming data signal to produce a sharply defined leading pulse edge. But the rising edge of the DATA clock waveform occurs while the RESET line is still high. Consequently, the clock signal applied to the flip-flop has no effect on its state, and the flip-flop remains reset to represent phase 2. As soon as the VSENSE line goes high, the RESET output of gate G3 goes low, but by this time the DATA clock line is high in potential and it is too late to clock the flip-flop. The system is once again in channel 0, phase 2, so that following the first data break the leading edge of the first data pulse can cycle the system to channel 1, phase 1.

In the second type of transmission scheme to be described below, carrier transmission does not stop between frames. This allows immediate stimulation control without having to wait during a power-up sequence. In this case, the system is held reset between frames in channel 0, phase 1 (not phase 2). Because the carrier is transmitted continuously, the voltage regulator output remains high as does the VSENSE line.

There is no reset pulse at all, and the system remains in channel 0, phase 1 because that is where the transmitter left it; following the data break which preceded placing the system in channel 0, phase 1, the transmission is continuous so that once the system is in channel 0, phase 1, it stays there.

But for proper synchronization, the system must somehow be cycled through channel 0, phase 2, to channel 1, phase 1. What is required in this case, therefore, is that a channel 0, phase 2 pulse be generated. All this entails is introducing a data break in the carrier, followed by another short carrier burst. This burst is treated as a data pulse and controls cycling of the system through phase 2 of channel 10. After the next data break, the leading edge which arrives represents the start of the first data pulse for channel 1, and the system is clocked to channel 1, phase 1 in the usual way.

But in such a case the TMAX time-out circuit might otherwise present a problem because it is difficult in practice to control the duration of TMAX precisely. The system is supposed to remain in non-stimulating channel 0, phase 1 between frames in the presence of continuous carrier. If the carrier persists for more than TMAX seconds, the NODATA line goes high; if it controlled a reset, the counter and flip-flop would be reset to channel 0, phase 2. To avoid such a reset and a loss of synchronization, the $\overline{CH0}$ input of gate G6 is provided. If the system is in channel 0, then even if the NODATA line goes high to indicate the presence of continuous RF, because the $\overline{CH0}$ input is low the NODATA output remains high so that a reset pulse is not generated.

There is no need to be concerned with excessive stimulation during channel 0 because all of the electrodes are shorted together at this time. The only time that the fail-safe feature of the system is required is if there is continuous carrier while the system is in some channel other than channel 0. At this time the $\overline{CH0}$ input to gate G6 is high, and the NODATA output can be generated to control a reset if the carrier persists for longer than TMAX seconds. This kind of reset is shown in waveforms 3E, 3F, and 3G; assuming that continuous carrier is received while the system is operating in channel 5 (see waveform 30), the NODATA signal is generated to control a reset, with the system being placed in channel 0, phase 2 (Q output of flip-flop FF1 low).

The system is so flexible in the transmission formats which it allows that deliberately controlled "fault" conditions of this type can actually be used to separate frames. As shown in FIG. 3, a frame may be terminated simply by transmitting the carrier for TMAX seconds without a data break, following which there is a reset and cycling begins with channel 1, phase 1—after the next data break. Such a scheme is not preferred, however, because the last channel operated on in the frame has to be stimulated for TMAX seconds.

Capacitor C2, in addition to serving as a filter for the power supply, provides the additional function of power-down detection. The VSENSE signal has been described thus far as controlling resetting of the counter at the start of any frame transmission (power-up) and at the end of any frame transmission (power-down). Such synchronization is necessary if an intermittent transmission scheme is employed; a frame of information is transmitted only when stimulation is required, and between frames there is no transmission. A power-down condition is detected by sensor 16 determining that the potential across capacitor C2 has dropped below a threshold value. When tranmission ceases, capacitor C2 discharges through any resistance which is then connected across the outputs of voltage regulator 12.

The time constant must be such that the capacitor does not discharge to the point at which the VSENSE line goes low during the normal 2-microsecond separation between pulses. Otherwise, power-down conditions would be detected all the time. On the other hand, the capacitor should not take too long to discharge because a true power-down condition should be detected as soon as possible so that the system may reset with all of the electrodes being shorted together. For capacitor C2 to function as a reliable timer, a load must be placed across it so that it can discharge with a predetermined time constant. The function of gates G4 and G5, and transistor FET2, is to place load resistor R3 in the circuit so that capacitor C2 can discharge through it and the voltage regulator whenever power-down timing is required.

Such power-down timing is required whenever the carrier ceases, e.g., with a data break or at the end of a frame. In such a case, the $\overline{DATA}$ line input of gate G4 goes high so that one input of gate G5 is held low. As soon as carrier transmission ceases, the output of sensor 16 is still high and thus the $\overline{VSENSE}$ input of gate G5 is also low. With both inputs of the gate low its output is high, transistor FET2 conducts, and load resistor R3 is placed in the circuit so that capacitor C2 can function as a reliable timer. After the time-out (in excess of the maximum interpulse gap), the VSENSE line goes low and gate G3 generates a reset pulse.

Since the system is now reset, there is no need to allow continued discharge of capacitor C2. This would not only be wasteful of power, but it would require a longer time at the beginning of the next frame for the capacitor to recharge and for the VSENSE line to go high again. It is for this reason that the $\overline{VSENSE}$ line is connected to an input of gate G5. As soon as the output of sensor 16 goes low and the VSENSE line goes high, transistor FET2 is turned off so that whatever charge remains on capacitor C2 is not dissipated (except for the normally high internal impedances which may be present in the integrated circuit on which the system is fabricated and which prevent perpetual charge storage). While it is not essential for charge to be maintained across capacitor C2 between frames, it is desirable that it persist for at least some short time after the system is reset, i.e., that the potential remain high enough to power the logic. With the system reset the electrodes are shorted together, and they should remain shorted in this way for a sufficient length of time to allow charge recovery.

Even during the scanning of channels 1–15, capacitor C2 functions as a timer so that the system may be reset and the electrodes shorted together should it be necessary. During active channel scanning, the connected electrodes (whichever pair is being energized) serve as load resistors. It is only when there are no connected electrodes that resistor R3 must be placed in the circuit. This occurs during a data break; between successive pairs of pulses and between the two pulses in any pair, all of the electrodes are open-circuited. The function of the $\overline{DATA}$ input of gate G4 is to place resistor R3 in the circuit at such a time. But when the system is operating in channel 0, there are also no connected electrodes. Thus in this case also resistor R3 should be placed in the circuit (so that the C2/R3 time-out will place the system in phase 2 of channel 0 should it be in phase 1 of channel 0). At such a time the CH0 line is high to energize the second input of gate G4. When this input is high it controls the turning on of transistor FET2, just as does the high potential on the DATA input.

It should be noted that in single-chip implementation, impedance R3 would in face consist of an active device set up as a load resistor.

Thus far what have been described are the signals which control the resetting of counter 20. The counter has 16 states, the first of which controls the shorting together of all electrodes. Each of the other fifteen states controls the application of a biphasic pulse to a respective pair of electrodes. How the counter controls the selection of a particular pair of electrodes or the shorting together of all of them, and how the widths of any pair of electrode pulses is controlled by the widths of a pair of data pulses in the transmitted signal will be described below. But before proceeding to a description of the circuitry involved, it will be helpful to consider further the two transmission schemes discussed above; these schemes are depicted in FIGS. 6A and 6B. An understanding of the two schemes will convey the great flexibility of the system, and the manner in which the prosthesis allows widely varying stimulation strategies and transmission schemes to be employed.

Figure 6A:
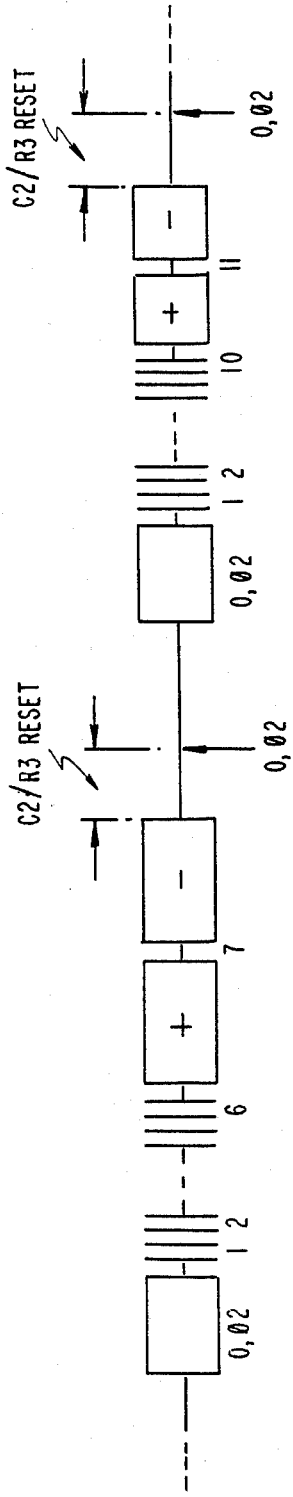
FIG. 6 depicts two alternative transmission schemes which may be utilized with the system of FIGS. 1 and 2.

In the scheme of FIG. 6A, the carrier is not transmitted between frames, and during each frame only a single site is stimulated. At the end of any frame, the VSENSE line goes low and a reset pulse is generated. This causes counter 20 to be reset to represent channel 0, and flip-flop FF1 to be reset to represent phase 2.

At the start of the next frame, there may or may not be sufficient charge left on capacitor C2 to power the logic. But as described above, the initial power-up carrier burst either leaves the system in channel 0, phase 2 if it was there, i.e., the logic is still powered, or it places the system in this same state by controlling a reset, i.e., the logic is not still powered. In FIG. 6A, the initial carrier burst is shown as controlling state "0, $\emptyset2$"—channel 0, phase 2.

As shown in FIG. 3A, at the end of the initial period of carrier transmission, there is a data break of 2 microseconds, followed by the leading edge of the first data pulse. On the rising edge of this pulse, flip-flop FF1 is clocked. Since its $\overline{Q}$ output, which is high during phase 2, is fed back to the D input, the Q output now goes high while the $\overline{Q}$ output goes low; phase 1 is now represented. The positive edge at the CK input of counter 20 and the negative edge at the $\overline{CK}$ input cause the counter to advance to channel 1. After the first pulse of channel 1, there is a data break followed by the rising edge of the second pulse of channel 1. The flip-flop is clocked once again and because the $\overline{Q}$ output is low, it is the Q output which now goes low and the $\overline{Q}$ output which now goes high. These polarity signals do not advance counter 20. The counter is advanced once again only with the rising edge of the first pulse in the second pair of data pulses.

As shown in waveform 3G, during the initial portion of the transmission flip-flop FF1 remains reset and the Q output remains low. The initial step on the DATA clock line does not clock the flip-flop as described above. It is only after the initial power-up transmission, during which capacitor C2 charges, that the flip-flop is clocked at the start of the first data pulse. Counter 20 is advanced at the start of each pair of data pulses, when the flip-flop is toggled to represent phase 1.

While the system is reset, the $\overline{CH0}$ line is low and one input of each of gates G1 and G2 is held low. Consequently, the $\overline{\emptyset1}$ and $\overline{\emptyset2}$ lines are both held high as shown in waveforms 3H and 3I. But at the leading edge of the first data pulse, the flip-flop is clocked and its Q output goes high. As soon as the counter advances to channel 1, the $\overline{0}$ output of decoder 22 goes high and the $\overline{1}$ output goes low. Neither of gates G1 and G2 is now disabled by the $\overline{CH0}$ line. There is still a low input to gate G2 because the $\overline{Q}$ output of the flip-flop is low. But gate G1 is now enabled because its input is connected to the Q output of the flip-flop which is high. The third input of each of gates G1 and G2 is connected to the DATA line. It is thus apparent that during the first pulse of the first pair of data pulses, the output of gate G1 is low for the duration of the pulse. This is shown in waveform 3H. During the data break between the two pulses in the first pair, the outputs of gates G1 and G2 are both high because the DATA line is low. But the leading edge of the second pulse in the first pair clocks the flip-flop once again so it is now gate G2 which is enabled rather than gate G1. With the DATA line high, it is the $\overline{\emptyset2}$ output which goes low and remains low for the duration of the second pulse in the first pair. Because the two pulses in each pair have the same width in the illustrative embodiment of the invention, the first pulse in both of the $\overline{\emptyset1}$ and $\overline{\emptyset2}$ waveforms are shown having the same width. Both pulses occur while the $\overline{1}$ output of decoder 22 is low, depicted by waveform 3K. (Waveforms 3J-3O simply depict the channel being operated upon at any time; while the CH0 signal is "real", there are no CH1-CH5 signals generated in the system.)

As each pair of data pulses arrives, the flip-flop cycles and the counter is advanced. For each count, a different decoder output is low for the duration of the transmitted pulse pair—from the start of the first pulse in the pair until the start of the first pulse in the next pair—but the $\overline{\emptyset1}$ and $\overline{\emptyset2}$ outputs are low only for the durations of respective ones of the two pulses. FIG. 3 depicts the manner in which successive sites are stimulated, the duration of each stimulation depending upon the widths of the two pulses in the respective pair.

FIG. 6A shows the system in phase 2 of channel 0 at the start of the frame transmission, as described. In the illustrated transmission format, the two pulses in each of channels 1–6 are very short. (The pulse widths of FIGS. 3 and 6 are different.) Although the $\overline{\emptyset1}$ and $\overline{\emptyset2}$ lines go low and actually control site stimulation, the stimulation is so short that it is not perceived. The ineffective stimulations are shown in the drawing by vertical line segments for each of the pulses.

At the start of the seventh data pulse pair, the same type of operation takes place when the $\overline{7}$ output of decoder 22 goes low. But the two pulses in this pair are wider. In FIG. 6A, the first pulse is shown as being negative and the second is shown as being positive only to indicate that the two stimulations are of opposite polarity.

In the transmission scheme of FIG. 6A, only one channel is stimulated during any frame, and the carrier transmission ceases abruptly at the end of the second pulse associated with that channel. The system does not cycle through channels which do not require stimulation following the channel which does; cycling through channels which do not require stimulation occurs only for those which are lower than the channel which requires stimulation (in order to count to the desired channel). As indicated in FIG. 6A, as soon as the transmission ceases, resistor R3 is placed in the circuit because the DATA line is high while the $\overline{VSENSE}$ line is still low. Capacitor C2 discharges through the resistor until the VSENSE line goes low. At this time, a reset pulse is generated and the system is reset in channel 0, phase 2, as depicted in FIG. 6A and also at the end of the CH0 waveform of FIG. 3J. As described above, in FIG. 3 the voltage regulator output waveform is shown as decaying relatively rapidly after the cessation of transmission. In such a case, the RESET line goes high at the end of the frame when the VSENSE line goes low; the RESET line goes high once again at the start of the next frame. On the other hand, if the next frame begins before the voltage regulator output has fallen so that the VSENSE line goes high, the RESET output of gate G3 remains high between frames. It makes no difference from an operational point of view, however, whether the system is held in channel 0, phase 2 between frames, or is placed in this state at the start of each frame; what is important is that between frames, if the system is still powered, the counter should be reset.

The waveform of FIG. 6A depicts the reset in channel 0, phase 2 after the C2/R3 time-out. The second frame depicted in this waveform shows a similar cycle, but with channel 11 being stimulated instead of channel 7. In all other respects, the operation is the same.

Figure 6B:
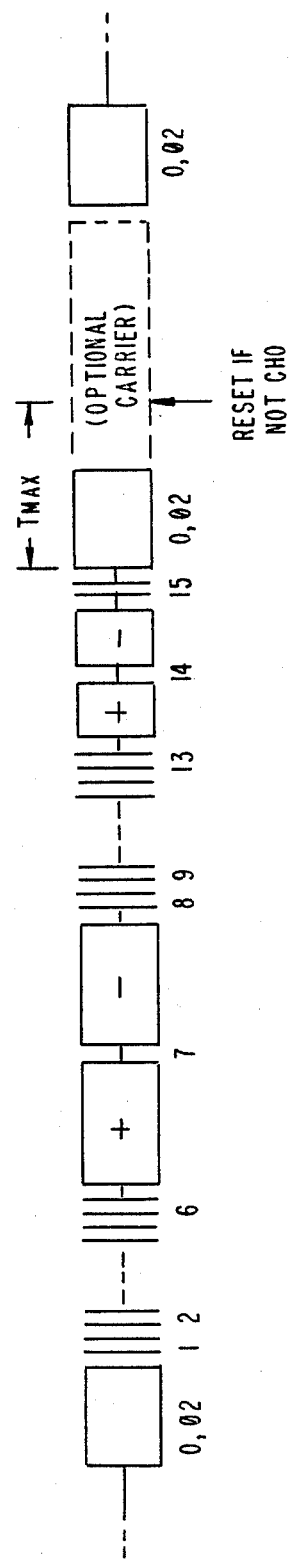

In the scheme of FIG. 6B, not only can multiple channels be stimulated in a single frame, but the system cycles through all fifteen channels during each frame—even through the channels at the end, after the last channel which requires stimulation. Also, the carrier is transmitted even when stimulation is not required. Assuming that the system is initially in channel 0, phase 2, the cycling is the same as that described for the scheme of FIG. 6A, through channel 7. But instead of terminating the frame at this point, channels 8–13 are rapidly cycled, following which channel 14 is stimulated as required. Channel 15 is then gone through rapidly. Following the data break after the second 4-microsecond data pulse in the pair associated with channel 15, the carrier is transmitted once again. A reset pulse is not generated because the VSENSE line does not go low. Instead, the counter cycles from state 15 to state 0, and the flip-flop clocks in the usual way so that channel 0, phase 1 (not phase 2) is represented.

The width of the pulse which persists while the system is in channel 0, phase 1 is arbitrary, and this is indicated by the notation "optional carrier". If the carrier persists, the VSENSE line does not go low. A short break prior to the next frame, followed by a carrier burst, toggles flip-flop FF1 to phase 2, as shown in FIG. 6B. At the end of this initial burst, a data break followed by a data pulse starts the system operation in channel 1, phase 1. On the other hand, if the carrier is not transmitted continuously between frames and there is a long inter-frame gap, the system will reset in the usual way when the VSENSE line goes low. If the gap is long enough such that all power is lost, the carrier burst at the start of the next frame sets the system in channel 0, phase 2 as described above in connection with the waveforms of FIG. 3, so that the first data pulse controls operation in channel 1, phase 1.

But suppose the gap is long enough to allow the VSENSE line to go low (a reset condition), but not long enough to cut off power to the logic elements. The system is placed in channel 0, phase 2. Because the RESET line remains high, as described above in connection with the waveforms of FIG. 3, the initial carrier burst at the start of the next frame leaves the system in channel 0, phase 2 so that proper cycling ensues.

Lastly, consider the case in which the logic remains powered until the start of the next frame, with the system being in channel 0, phase 1, but the carrier is transmitted for longer than TMAX seconds between frames. If the TMAX time-out were allowed to control a reset to channel 0, phase 2, and since the carrier break before the next frame is typically not long enough to allow the VSENSE line to go low (in order to place the system reset in channel 0, phase 2 at the start of the next frame), the RESET line would be low at the start of the next frame and the initial carrier burst would cycle the system to channel 1, phase 1 before arrival of the first data pulse; synchronization would be lost. It is for this reason that the CH0 input to gate G6 prevents a TMAX time-out reset if the system is in channel 0. The system remains in channel 0, phase 1—even if there is a TMAX time-out—and at the start of the next frame it is cycled through phase 2, as required.

Thus it is apparent that maximum flexibility is achieved because the prosthesis works properly no matter what the length of carrier transmission between frames.

Referring back to FIGS. 1 and 2, it has already been described how flip-flop FF1 is clocked and how the switching of the flip-flop from representing phase 2 to representing phase 1 controls advance of counter 20. The counter itself is conventional in that it has four stages. The least significant stage causes its A output to be low and its $\bar{A}$ output to be high when it represents a 0, and the A output to be high and the $\bar{A}$ output to be low when it represents a 1. Similar remarks apply to the three other stages, with each stage advancing when the preceding stage switches from a 1 to a 0. The 4-bit to 16-line decoder 22 is of conventional design. Depending upon the states of the four double-rail inputs, one of sixteen output lines is forced low. A circuit for implementing the decoder is shown in FIG. 4 and its operation will be apparent to those skilled in the art without any further description, especially since such circuits can be purchased in chip form.

It has also been described how gates G1 and G2 control the $\bar{\phi}1$ and $\bar{\phi}2$ outputs to be high when the system is in channel 0 (CH0 line low), and how these gates are enabled to operate only when decoder 22 represents one of the channels 1–15. Which of the two gates forces its output low depends on the state of flip-flop FF1, the gate output going low for as long as the respective data pulse is received.

The circuitry at the bottom of FIG. 2 is symbolic only. Sixteen output circuits are depicted for energizing 16 electrodes E1–E16. Successive pairs of these electrodes define fifteen stimulation sites. All sixteen electrodes are to be shorted together with the CH0 line is high (channel 0), and it is for this reason that the line is connected to each of the sixteen output circuits. Each pair of output circuits is connected to a respective one of the $\overline{1\text{-}15}$ outputs of decoder 22, so that a pair of output circuits may be energized when each channel is being operated upon. It should be noted that except for the first and last output circuits, each output circuit is connected to two of the decoder outputs since all of electrodes E2–E15 are involved in the stimulations at two different sites. Only the output circuits associated with electrodes E1 and E16 are associated with respective single sites. The $\bar{\phi}1$ and $\bar{\phi}2$ outputs are also extended to each of the output circuits since it is the width of the pulse on each of these lines which actually controls the length of operation of a pair of output circuits; the output circuits in the pair which is operated have relative polarities depending upon which of the $\overline{\phi 1}$ and $\overline{\phi 2}$ lines is low, i.e., the phase of the biphasic pulse being generated.

FIG. 5A depicts any one (the Nth) of the intermediate output circuits associated with electrodes EN. The circuit has five inputs. The first is an input which represents channel 0, the CH0 line in FIG. 2. This line is high whenever channel 0 is selected. In the drawing of FIG. 5A, the output circuit depicted is associated with channel N. Thus the two inputs connected to this circuit from decoder 22 are the $\overline{N}$ and $\overline{N-1}$ outputs of the decoder. Referring to FIG. 2, it will be noted that any electrode EN is selected for operation when decoder outputs $\overline{N}$ and $\overline{N-1}$ go low. The last two inputs are the $\overline{\phi 1}$ and $\overline{\phi 2}$ lines which are common to all of the electrode drivers. The output stage of the circuit consists of a pair of complementary FET transistors 54, 56 which are connected across the power supply, as shown. At the junction of the two transistors a connection is made to electrode EN.

When the system is in channel 0, the $\overline{CH0}$ line is low to force the outputs of gates G1 and G2 to remain high. Thus with the $\overline{\phi 1}$ and $\overline{\phi 2}$ lines both high in FIG. 5A, the outputs of all of gates 40, 42, 44 and 46 are low. Because both inputs of gate 50 are low, its output is high and the output of inverter 52 is low. Consequently, transistor 56 remains off. Although two of the inputs of gates 48 are also low, the channel 0 input (the CH0 line in FIG. 2) is high, and thus the output of gate 48 is low to hold transistor 54 on. Consequently, electrode EN is shorted through its respective transistor 54 to the positive supply line, along with all of the other electrodes—the required operation in channel 0. By thus shorting all electrodes in the absence of the need to stimulate a site, it is not necessary to provide the usual AC-coupling output capacitors for minimizing net charge delivery and cancelling electrode polarization currents.

When any other channel is being operated upon, the channel 0 input can be ignored because it is low and has no effect on gate 48.

Between the two pulses in any pair, or between the last pulse of one pair and the first of the next, both of the $\overline{\phi 1}$ and $\overline{\phi 2}$ lines are high in potential since one input of each of gates G1 and G2 is connected to the DATA line which is low whenever there is a data break. Consequently, at least one input of each of gates 40, 42 44 and 46 is high in potential and the outputs of all of the gates are low. All of the inputs to gate 48 and 50 are thus low. As a result, the output of gate 48 is high and the output of inverter 52 is low. Both of transistors 54 and 56 are held off so that electrode EN floats. This is what is desired during any data break when the system is not in channel 0. It is also the reason for switching resistor R3 (FIG. 1) into the circuit at this time, since there is no other load impedance which is placed across capacitor C2 which would allow it to function as a reliable timer.

If electrode EN is not one of the two involved in stimulation at a site whose respective channel is represented by counter 20, then both of the N and $\overline{N-1}$ inputs to the circuit of FIG. 5A are high in potential. Even though one of the $\overline{\phi 1}$ and $\overline{\phi 2}$ inputs may go low, one of the $\overline{N}$ and $\overline{N-1}$ inputs is connected to an input of each of gates 40, 42, 44 and 46. With one input of each gate held high, the operation is the same as it is when the $\overline{\phi 1}$ and $\overline{\phi 2}$ lines hold one input of each gate high; the two output transistors do not conduct and the respective electrode is not involved in the stimulation.

Suppose now that site N is to be stimulated. During the first phase electrode EN should be connected to the negative side of the supply (when the $\overline{\phi 1}$ line is low), and during the second phase it should be connected to the positive side of the supply (when the $\overline{\phi 2}$ line is low)—in order that a biphasic pulse be produced. When site N is being stimulated the $\overline{N}$ input is low. During phase 1, both inputs of gate 46 are low and its output is high. Consequently, the output of gate 50 is low, the output of inverter 52 is high and transistor 56 is held on. The $\overline{\phi 2}$ input of gate 40 is high and the $\overline{N-1}$ input of gate 42 is high, so both of the gate outputs are low. Consequently, the output of gate 48 is high and transistor 54 is held off; only transistor 56 conducts to connect electrode EN to the negative side of the supply. During phase 2 of the same channel, the $\overline{\phi 1}$ input of gate 46 and the $\overline{N-1}$ input of gate 44 are both high, both gate outputs are low, the output of gate 50 is high and the output of inverter 52 is low so that transistor 56 is held off. While the output of gate 42 is low since its $\overline{\phi 1}$ input is high, the output of gate 40 is now high because both of its $\overline{N}$ and $\overline{\phi 2}$ inputs are low. The output of gate 48 is thus low to control conduction in transistor 54. Consequently, electrode EN is connected to the positive side of the supply.

It is when the preceding channel $\overline{N-1}$ is selected that the reverse operation must take place. During phase 1 electrode EN should be coupled to the positive side of the supply, and during phase 2 it should be coupled to the negative side of the supply. When the $\overline{N}$ input being high, the outputs of gates 40 and 46 are low, and they can be ignored. During phase 1, the $\overline{\phi 2}$ input is high, the output of gate 44 is low along with the output of gate 46, the output of gate 50 is high, and transistor 56 is held off. But because both inputs of gate 42 are low, its output is high to control conduction in transistor 54. Conversely, during phase 2, it is the two inputs of gate 44 which are low, the output of gate 50 goes low, and transistor 56 conducts rather than transistor 54 to connect electrode EN to the negative side of the supply.

FIG. 5B depicts the output stage for electrode E1. This electrode must be selected only during channel 1. During phase one of this channel, electrode EN should be connected to the negative side of the supply and during phase 2 it should be connected to the positive side of the supply. (During both phases, the output circuit associated with electrode E2 controls opposite polarity connections.) In channel 0, the channel 0 input of gate 64 is high so that its output is low to hold transistor 66 on; electrode E1 is shorted through the transistor to the positive side of the supply, to which all of the other electrodes are connected at the same time. Since the $\overline{1}$ input is high in channel 0, the output of gate 62 is low so that transistor 68 remains off. When operating in any channel other than channel 1, the channel 1 input is high. The output of gate 62 is low to hold transistor 68 off; the output of gate 60 is low, together with the channel 0 input, and the output of gate 64 is high to hold transistor 66 off. Between pulses, both of the $\overline{\phi 1}$ and $\overline{\phi 2}$ lines are high, so that the outputs of gates 60 and 62 are low. With the two inputs of gate 64 both being low, its output is high to hold transistor 66 off, and with the output of gate 62 being low, transistor 68 is held off; electrode E1 floats as required.

But if channel 1 is selected, the $\overline{1}$ input is low. During phase 1, the $\overline{\phi 1}$ input is low. With both inputs to gate 62 being low, its output is high to control conduction in transistor 68. Because the $\overline{\phi 2}$ input is high, the output of gate 60 is low so that transistor 66 remains off. Conversely, during phase 2 of channel 1, it is the output of gate 60 which is high while the output of gate 62 is low, so that transistor 66 conducts rather than transistor 68.

FIG. 5C depicts the output stage associated with electrode E16. In channel 0, the channel 0 input of gate 74 is high so that its output is low to hold transistor 76 on; since the $\overline{15}$ input is high, the output of gate 72 is low to hold transistor 78 off. Between data pulses, the $\overline{\phi 1}$ and $\overline{\phi 2}$ lines are both high so that the outputs of gates 70 and 72 are both low, to hold both of the output transistors off. In any active channel other than channel 15, the $\overline{15}$ input is high so that the outputs of both gates 70 and 72 are low. The low output of gate 72 holds transistors 78 off, and because both inputs of gates 74 are low its output is high to hold transistor 76 off.

In channel 15, however, the 15 input is low and has no effect on gates 70 and 72. During phase 1 of channel 15, the $\overline{\phi 1}$ input is low and with both inputs of gate 70 low, its output is high to hold transistor 76 on. Because the $\overline{\phi 2}$ input is high, the output of gate 72 is low to hold transistor 78 off. This is as required because the sixteenth output circuit, which is selected only in channel 15, must connect electrode E16 to the positive supply during phase 1. During phase 2 of channel 15, it is both inputs of gate 72 which are low and its output is high. Transistor 78 now conducts to connect electrode E16 to the negative side of the supply. Because the $\overline{\phi 1}$ input is high, the output of gate 70 is low to hold transistor 76 off.

In the prior art, pulse amplitude has been varied as well as pulse width for auditory nerve stimulation. The intensity of a response to electrical stimulation is related to the charge delivered, and the amount of charge delivered can be controlled by either or both of current amplitude and pulse width. Although the response is not exactly proportional to the integral of the pulse, it is the view of some investigators that while varying either pulse amplitude or pulse width is an effective means of controlling perceived intensity, the two techniques are not equivalent and the percepts resulting from them are different in quality. One explanation of this phenomenon is that for a very short pulse all nerve endings whose thresholds are exceeded will fire synchronously, whereas for a longer, lower-amplitude pulse various groups of nerve endings will fire as their respective thresholds are exceeded at different times during application of the pulse. Because the auditory decoding mechanisms in the ascending auditory pathway and the cortex is capable of very fine temporal discrimination, a different sound may be perceived. Thus while the illustrative embodiment of the invention is designed to vary pulse width only, it is recognized that it may be advantageous to also employ a form of pulse amplitude control at the same time or even by itself in order to control pulse intensity.

The principles of our invention are equally applicable to systems which utilize pulse-amplitude or some other type of control, either by itself or in conjunction with pulse-width control. Such a system would still utilize a number of electrodes approximately equal to the number of stimulation sites, with biphasic pulses being produced by switching the polarities of a pair of electrodes at each site; pairs of electrodes would still define respective stimulation sites, with at least almost all of the electrodes being included in each of two different pairs. It is also possible for each electrode to be included in each of three or more different pairs. The stimulation sequence would still be sequential, with only a single site being stimulated at a single instant of time even though "simultaneous" stimulations would be perceived if the channel switching is fast enough. Similarly, for simplicity of operation the system would cycle through all channels below that associated with a site to be stimulated, the rapid cycling through the lower channels resulting in stimulations which cannot be perceived. The same transmission formats can be used, and the same resetting and failsafe features could be provided.

Should the only control be over pulse amplitude, a pulse-width modulation scheme could still be employed. A pulse amplitude could be derived by using an analog technique to integrate each pulse, or an additional counter could be provided for measuring the duration of each received pulse and converting it to an amplitude. For example, the number of carrier cycles which comprise each pulse could be counted. The final count would be used to set the amplitude.

The same principles of our invention can be applied to systems which control both pulse width and pulse amplitude. In such a case, the two pulses in each channel might not directly control different phases of the respective biphasic pulse. Instead, the width of the first pulse in any channel might represent a stimulation pulse width, and the width of the second pulse in any channel might represent the stimulation pulse amplitude. Both values would be stored, and only after transmission of the two channel pulses would the biphasic stimulation pulse be generated by the prosthesis, with the two halves of the pulse having opposite polarities but the same amplitude and width, depending upon the two stored values for the respective channel. Alternatively, information represented within the channel 0 interval could be used to set the amplitude of all pulses generated during the succeeding frame. Although it is not now known whether anything is even to be gained by controlling both amplitude and width of the stimulation pulses, it should be understood that the principles of our invention are not limited to either scheme alone.

Although the invention has been described with reference to a particular cochlear prosthesis, it is to be understood that the principles of the invention are applicable not only to other types of prostheses, but that the cochlear embodiment disclosed is merely illustrative of the principles of the invention. Numerous modifications may be made therein and other arrangements may be devised without departing from the spirit and scope of the invention.

What we claim is:

1. A cochlear prosthesis comprising a plurality of electrodes, pairs of which are associated with respective stimulation sites and with at least almost all of said electrodes being included in each of at least two different pairs, means for detecting a transmitted information signal which represents both stimulation sites and stimulation intensities required therefor, and means under control of said detecting means for energizing the pair of electrodes associated with a represented stimulation site with successive opposite-polarity current pulses in accordance with the respective represented stimulation intensity, said energizing means energizing only a single pair of electrodes at any instant of time and operating fast enough such that at least any two electrode pairs can be energized successively within the time interval that allows the respective site stimulations to be perceived as occurring simultaneously.

2. A cochlear prosthesis in accordance with claim 1 wherein said time interval is less than one millisecond.

3. A cochlear prosthesis in accordance with claim 1 wherein said information signal represents a stimulation intensity in the form of a pulse width.

4. A cochlear prosthesis in accordance with claim 3 wherein said information signal is formatted in successive frames with each frame including a plurality of pulses in a predetermined sequence corresponding to respective stimulation sites, and said energizing means is capable of energizing successive pairs of electrodes in a predetermined sequence corresponding to the predetermined pulse sequence in each frame.

5. A cochlear prosthesis in accordance with claim 4 wherein in order to energize the electrode pair associated with a stimulation site represented in any frame said energizing means first cycles through and selects for energization all electrode pairs which are earlier in said predetermined sequence, any such earlier selected electrode pair which is associated with a stimulation site which does not require perceptible stimulation not being energized by said energizing means with current pulses which can be perceived.

6. A cochlear prosthesis in accordance with claim 5 wherein successive pairs of electrodes in said predetermined sequence have an electrode in common.

7. A cochlear prosthesis in accordance with claim 6 further including means for shorting together of all of said electrodes, and means for operating said shorting means after said energizing means has operated on all of the electrode pairs represented in an information signal frame.

8. A cochlear prosthesis in accordance with claim 6 further including means for shorting together all of said electrodes, means for detecting a pulse width in said information signal which exceeds a predetermined width, and means responsive to operation of said pulse width detecting means for operating said shorting means.

9. A cochlear prosthesis in accordance with claim 6 wherein a stimulation site is represented in an information signal frame by a respective pair of successive pulses, and said energizing means controls the intensity of each of the opposite-polarity current pulses applied to a represented stimulation site in accordance with the width of a different one of the respective pair of pulses.

10. A cochlear prosthesis in accordance with claim 9 wherein said energizing means includes means for switching the polarity of a single source of power across any electrode pair for deriving opposite-polarity current pulses.

11. A cochlear prosthesis in accordance with claim 6 further including means for deriving a source of power for said detecting and energizing means from the detected information signal.

12. A cochlear prosthesis in accordance with claim 11 further including means for shorting together all of said electrodes, means for detecting a predetermined drop in the level of said source of power, and means responsive to said level drop detecting means for operating said shorting means.

13. A cochlear prosthesis in accordance with claim 6 further including means for inhibiting the energizations of all of said electrodes, means for determining if the detected information signal is inconsistent with a predetermined format, and means responsive to operation of said determining means for operating said inhibiting means.

14. A cochlear prosthesis in accordance with claim 13 wherein said inhibiting means is further operative to short together all of said electrodes.

15. A cochlear prosthesis in accordance with claim 13 further including means for re-synchronizing the operation of said energizing means to successive information signal frames, and means responsive to said determining means for controlling operation of said re-synchronizing means.

16. A cochlear prosthesis in accordance with claim 4 further including means for shorting together of all of said electrodes, and means for operating said shorting means after said energizing means has operated on all of the electrode pairs represented in an information signal frame.

17. A cochlear prosthesis in accordance with claim 4 further including means for shorting together all of said electrodes, means for detecting a pulse width in said information signal which exceeds a predetermined width, and means responsive to operation of said pulse width detecting means for operating said shorting means.

18. A cochlear prosthesis in accordance with claim 4 wherein a stimulation site is represented in an information signal frame by a respective pair of pulses, and said energizing means controls the intensity of each of the opposite-polarity current pulses applied to a represented stimulation site in accordance with the width of a different one of the respective pair of pulses.

19. A cochlear prosthesis in accordance with claim 18 wherein said energizing means includes means for switching the polarity of a single source of power across any electrode pair for deriving opposite-polarity current pulses.

20. A cochlear prosthesis in accordance with claim 4 wherein said energizing means including means for switching the polarity of a single source of power across any electrode pair for deriving opposite-polarity current pulses.

21. A cochlear prosthesis in accordance with claim 4 further including means for deriving a source of power for said detecting and energizing means from the detected information signal.

22. A cochlear prosthesis in accordance with claim 21 further including means for shorting together all of said electrodes, means for detecting a predetermined drop in the level of said source of power, and means responsive to said level drop detecting means for operating said shorting means.

23. A cochlear prosthesis in accordance with claim 4 further including means for inhibiting the energizations of all of said electrodes, means for determining if the detected information signal is inconsistent with a predetermined format, and means responsive to operation of said determining means for operating said inhibiting means.

24. A cochlear prosthesis in accordance with claim 23 wherein said inhibiting means is further operative to short together all of said electrodes.

25. A cochlear prosthesis in accordance with claim 23 further including means for re-synchronizing the operation of said energizing means to successive information signal frames, and means responsive to said determining means for controlling operation of said re-synchronizing means.

26. A cochlear prosthesis in accordance with claim 1 wherein said information signal is formatted in successive frames with each frame including a plurality of items of data in a predetermined sequence corresponding to respective stimulation sites, and said energizing means is capable of energizing successive pairs of electrodes in a predetermined sequence corresponding to the predetermined items of data sequence in each frame.

27. A cochlear prosthesis in accordance with claim 26 wherein in order to energize the electrode pair associated with a stimulation site represented in any frame said energizing means first cycles through and selects for energization all electrode pairs which are earlier in said predetermined sequence, any such earlier selected electrode pair which is associated with a stimulation site which does not require perceptible stimulation not being energized by said energizing means with current pulses which can be perceived.

28. A cochlear prosthesis in accordance with claim 26 wherein successive pairs of electrodes in said predetermined sequence have an electrode in common.

29. A cochlear prosthesis in accordance with claim 1 wherein a stimulation site is represented in said information signal by a respective pair of pulses, and said energizing means controls the intensity of each of the opposite-polarity current pulses applied to a represented stimulation site in accordance with the width of a different one of the respective pair of pulses.

30. A cochlear prosthesis in accordance with claim 29 wherein said energizing means includes means for switching the polarity of a single source of power across any electrode pair for deriving opposite-polarity current pulses.

31. A cochlear prosthesis in accordance with claim 1 wherein said energizing means includes means for switching the polarity of a single source of power across any electrode pair for deriving opposite-polarity current pulses.

32. An implantable tissue-stimulating prosthesis comprising a plurality of electrodes, pairs of which are associated with respective stimulation sites and with at least most of said electrodes being included in each of at least two different pairs, means for detecting a transmitted information signal which represents stimulation intensities required for said stimulation sites, and means under control of said detecting means for energizing said electrode pairs in accordance with the operation of said detecting means, said energizing means energizing only a single pair of electrodes at any instant of time and operating fast enough such that at least any two electrode pairs can be energized successively within the time interval that allows the respective site stimulations to be perceived as occurring simultaneously.

33. An implantable tissue-stimulating prosthesis in accordance with claim 32 wherein said time interval is less than one millisecond.

34. An implantable tissue-stimulating prosthesis in accordance with claim 32 wherein said information signal represents a stimulation intensity in the form of a pulse width.

35. An implantable tissue-stimulating prosthesis in accordance with claim 34 wherein said information signal is formatted in successive frames with each frame including a plurality of pulses in a predetermined sequence corresponding to respective stimulation sites, and said energizing means is capable of energizing successive pairs of electrodes in a predetermined sequence corresponding to the predetermined pulse sequence in each frame.

36. An implantable tissue-stimulating prosthesis in accordance with claim 35 further including means for shorting together all of said electrodes, means for detecting a pulse width in said information signal which exceeds a predetermined width, and means responsive to operation of said pulse width detecting means for operating said shorting means.

37. An implantable tissue-stimulating prosthesis in accordance with claim 35 wherein a stimulation site is represented in an information signal frame by a respective pair of pulses, and said energizing means applies a pair of successive opposite-polarity current pulses to each electrode pair which is energized, and controls the intensity of each of said opposite-polarity current pulses in accordance with the width of a different one of the respective pair of information signal pulses.

38. An implantable tissue-stimulating prosthesis in accordance with claim 32 wherein said information signal is formatted in successive frames with each frame including a plurality of items of data in a predetermined sequence corresponding to respective stimulation sites, and said energizing means is capable of energizing successive pairs of electrodes in a predetermined sequence corresponding to the predetermined items of data sequence in each frame.

39. An implantable tissue-stimulating prosthesis in accordance with claim 38 wherein in order to energize the electrode pair associated with a stimulation site represented in any frame said energizing means first cycles through and selects for energization all electrode pairs which are earlier in said predetermined sequence, any such earlier selected electrode pair which is associated with a stimulation site which does not require perceptible stimulation not being energized by said energizing means with current pulses which can be perceived.

40. An implantable tissue-stimulating prosthesis in accordance with claim 38 wherein successive pairs of electrodes in said predetermined sequence have an electrode in common.

41. An implantable tissue-stimulating prosthesis in accordance with claim 32 further including means for shorting together all of said electrodes, and means for operating said shorting means in the absence of said detecting means detecting an information signal which represents a requirement for site stimulation.

42. An implantable tissue-stimulating prosthesis in accordance with claim 32 further including means for shorting together all of said electrodes, means for detecting a represented stimulation intensity in said information signal which exceeds a predetermined intensity, and means responsive to operation of said stimulation intensity detecting means for operating said shorting means.

43. An implantable tissue-stimulating prosthesis in accordance with claim 32 wherein a stimulation site is represented in said information signal by a respective pair of pulses, and said energizing means applies a pair of successive opposite-polarity current pulses to each electrode pair which is energized, and controls the intensity of each of the opposite-polarity current pulses in accordance with the width of a different one of the respective pair of information signal pulses.

44. An implantable tissue-stimulating prosthesis in accordance with claim 43 wherein said energizing means includes means for switching the polarity of a single source of power across any electrode pair for deriving opposite-polarity current pulses.

45. An implantable tissue-stimulating prosthesis in accordance with claim 32 wherein said energizing means includes means for switching the polarity of a single source of power across any electrode pair for deriving opposite-polarity current pulses.

46. An implantable tissue-stimulating prosthesis in accordance with claim 32 further including means for deriving a source of power for said detecting and energizing means from the detected information signal.

47. An implantable tissue-stimulating prosthesis in accordance with claim 46 further including means for shorting together all of said electrodes, means for detecting a predetermined drop in the level of said source of power, and means responsive to said level drop detecting means for operating said shorting means.

48. An implantable tissue-stimulating prosthesis in accordance with claim 32 further including means for inhibiting the energizations of all of said electrodes, means for determining if the detected information signal is inconsistent with a predetermined format, and means responsive to operation of said determining means for operating said inhibiting means.

49. An implantable tissue-stimulating prosthesis in accordance with claim 48 wherein said inhibiting means is further operative to short together all of said electrodes.

50. An implantable tissue-stimulating prosthesis in accordance with claim 48 further including means for re-synchronizing the operation of said energizing means to said information signal, and means responsive to said determining means for controlling operation of said re-synchronizing means.

51. A cochlear prosthesis comprising a plurality of electrodes associated with each other in pairs, means for detecting a transmitted information signal, said information signal being in the form of sequential frames each of which identifies required stimulation intensities for respective paired electrodes in a predetermined sequence, and means responsive to said detecting means for selecting and energizing at most a single electrode pair at any instant but for selecting all of the electrode pairs and energizing them with the required respective stimulation intensities in the same sequence in which the electrode pairs are identified in a frame of said information signal, said selecting and energizing means operating fast enough such that at least any two electrode pairs can be selected and energized successively within the time interval that allows the respective stimulations to be perceived as occurring simultaneously 52. A cochlear prosthesis in accordance with claim 51 wherein any electrode pair which does not require stimulation, but precedes some other electrode pair which does in said predetermined sequence, is identified in a frame which identifies said some other electrode pair as requiring stimulation.

53. A cochlear prosthesis in accordance with claim 52 wherein said selecting and energizing means selects each electrode pair which is identified in sequence in a frame, but prevents effective energization of any electrode pair which does not require stimulation with an intensity which can be perceived.

54. A cochlear prosthesis in accordance with claim 53 wherein each frame consists of a sequence of pulse widths corresponding to the required stimulation intensities for respective electrode pairs.

55. A cochlear prosthesis in accordance with claim 54 wherein there are two successive pulses for each electrode pair identified in a frame, and said selecting and energizing means energizes an electrode pair by applying a biphasic pulse thereto, each half of which has an intensity which is a function of the width of a respective one of the two corresponding frame pulses.

56. A cochlear prosthesis in accordance with claim 53 wherein successive pairs of electrodes in said predetermined sequence have an electrode in common.

57. A cochlear prosthesis in accordance with claim 51 further including means for deriving a source of power for said detecting means and said selecting and energizing means from the transmitted information signal.

58. A cochlear prosthesis in accordance with claim 57 further including means for shorting together all of said electrodes, means for detecting a predetermined drop in the level of said source of power, and means responsive to said level drop detecting means for operating said shorting means.

59. A cochlear prosthesis in accordance with claim 51 further including means for inhibiting the energization of all of said electrodes, means for determining if the detected information signal is inconsistent with a predetermined format, and means responsive to operation of said determining means for controlling operation of said inhibiting means.

60. A cochlear prosthesis in accordance with claim 59 wherein said inhibiting means is further operative to short together all of said electrodes.

61. A cochlear prosthesis in accordance with claim 59 further including means for re-synchronizing the operation of said selecting and energizing means to sequential information signal frames, and means responsive to operation of said determining means for controlling operation of said re-synchronizing means.

62. A cochlear prosthesis in accordance with claim 51 wherein said selecting and energizing means includes means for switching the polarity of a single source of power across any electrode pair to be energized for applying to said electrode pair a pair of opposite-polarity current pulses.

63. A cochlear prosthesis in accordance with claim 51 wherein said selecting and energizing means includes a counter which is advanced by detected frame information and whose count selects a respective electrode pair.

64. A cochlear prosthesis in accordance with claim 63 wherein said counter includes a reset state, and further including means responsive to said counter being reset for shorting together all of said electrodes.

65. A cochlear prosthesis in accordance with claim 64 further including means responsive to the detection of the end of a frame for resetting said counter.

66. A cochlear prosthesis in accordance with claim 64 further including means responsive to the detection of the start of a frame for resetting said counter.

67. A cochlear prosthesis in accordance with claim 64 further including means responsive to the detection in a frame of said information signal of any required stimulation intensity which exceeds a predetermined intensity for resetting said counter.

68. A cochlear prosthesis in accordance with claim 51 wherein each frame consists of a sequence of pulse widths corresponding to the required stimulation intensities for respective electrode pairs.

69. A cochlear prosthesis in accordance with claim 68 wherein there are two successive pulses for each electrode pair identified in a frame, and said selecting and energizing means energizes an electrode pair by applying a biphasic pulse thereto, each half of which has an intensity which is a function of the width of a respective one of the two corresponding frame pulses.

70. A cochlear prosthesis in accordance with claim 51 wherein successive pairs of electrodes in said predetermined sequence have an electrode in common.

71. A cochlear prosthesis in accordance with claim 51 wherein said selecting and energizing means includes means for switching the polarity of a single source of power across any electrode pair to be energized for applying to said electrode pair a pair of opposite-polarity current pulses.

72. A cochlear prosthesis in accordance with claim 51 wherein said time interval is less than one millisecond.

73. An implantable tissue-stimulating prosthesis comprising a plurality of electrodes for stimulating a plurality of stimulation sites, means for detecting a transmitted information signal, said information signal being in the form of sequential frames each of which identifies required stimulation intensities for respective stimulation sites in a predetermined sequence, means responsive to said detecting means for selecting and energizing said electrodes so that at most a single stimulation site is stimulated at any instant but for selecting and energizing the electrodes such that the stimulation sites are stimulated with the required respective stimulation intensities in the same sequence in which the stimulation sites are identified in a frame of said information signal, and means for shorting said plurality of electrodes responsive to the absence of the identification of a site which requires stimulation.

74. An implantable tissue-stimulating prosthesis in accordance with claim 73 wherein any stimulation site which does not require stimulation, but precedes some other stimulation site which does in said predetermined sequence, is identified in a frame which identifies said some other stimulation site as requiring stimulation.

75. An implantable tissue-stimulating prosthesis in accordance with claim 74 wherein said selecting and energizing means selects each stimulation site which is identified in sequence in a frame, but prevents effective energization of any stimulation site which does not require stimulation with an intensity which can be perceived.

76. An implantable tissue-stimulating prosthesis in accordance with claim 75 wherein each frame consists of a sequence of pulse widths corresponding to the required stimulation intensities for respective stimulation sites.

77. An implantable tissue-stimulating prosthesis in accordance with claim 76 wherein there are two successive pulses for each stimulation site identified in a frame, and said selecting and energizing means energizes a stimulation site by applying a biphasic pulse thereto, each half of which has an intensity which is a function of the width of a respective one of the two corresponding frame pulses.

78. An implantable tissue-stimulating prosthesis in accordance with claim 73 wherein each frame consists of a sequence of pulse widths corresponding to the required stimulation intensities for respective stimulation sites.

79. An implantable tissue-stimulating prosthesis in accordance with claim 78 wherein there are two successive pulses for each stimulation site identified in a frame, and said selecting and energizing means energizes a stimulation site by applying a biphasic pulse thereto, each half of which has an intensity which is a function of the width of a respective one of the two corresponding frame pulses.

80. An implantable tissue-stimulating prosthesis in accordance with claim 73 further including means for deriving a source of power for said detecting means and selecting and energizing means from the transmitted information signal.

81. An implantable tissue-stimulating prosthesis in accordance with claim 80 further including means for shorting together all of said electrodes, means for detecting a predetermined drop in the level of said source of power, and means responsive to said level drop detecting means for operating said shorting means.

82. An implantable tissue-stimulating prosthesis in accordance with claim 73 further including means for inhibiting the energizations of all of said electrodes, means for determining if the detected information signal is inconsistent with a predetermined format, and means responsive to operation of said determining means for controlling operation of said inhibiting means.

83. An implantable tissue-stimulating prosthesis in accordance with claim 82 wherein said inhibiting means is further operative to short together all of said electrodes.

84. An implantable tissue-stimulating prosthesis in accordance with claim 82 further including means for re-synchronizing the operation of said selecting and energizing means to sequential information signal frames, and means responsive to operation of said determining means for controlling operation of said re-synchronizing means.

85. An implantable tissue-stimulating prosthesis in accordance with claim 73 wherein said selecting and energizing means includes a counter which is advanced by detected frame information and whose count selects a respective stimulation site.

86. An implantable tissue-stimulating prosthesis in accordance with claim 85 wherein said counter includes a reset state, and further including means responsive to said counter being reset for shorting together all of said electrodes.

87. An implantable tissue-stimulating prosthesis in accordance with claim 86 further including means responsive to the detection of the end of a frame for resetting said counter.

88. An implantable tissue-stimulating prosthesis in accordance with claim 86 further including means repsonsive to the detection of the start of a frame for resetting said counter.

89. An implantable tissue-stimulating prosthesis in accordance with claim 86 further including means responsive to the detection in a frame of said information signal of any required stimulation intensity which exceeds a predetermined intensity for resetting said counter.

90. An implantable tissue-stimulating prosthesis in accordance with claim 85 further including means responsive to the detection of the end of a frame for resetting said counter.

91. An implantable tissue-stimulating prosthesis in accordance with claim 85 further including means responsive to the detection of the start of a frame for resetting said counter.

92. An implantable tissue-stimulating prosthesis in accordance with claim 85 further including means responsive to the detection in a frame of said information signal of any required stimulation intensity which exceeds a predetermined intensity for resetting said counter.

93. An implantable tissue-stimulating prosthesis in accordance with claim 73 wherein said selecting and energizing means operates fast enough such that at least any two stimulation sites can be selected and energized successively within the time interval that allows the respective stimulations to be perceived as occurring simultaneously.

94. An implantable tissue-stimulating prosthesis in accordance with claim 93 wherein said time interval is less than one millisecond.

95. An implantable tissue-stimulating prosthesis comprising a plurality of electrodes, means for detecting a transmitted signal which represents the manner in which said electrodes are to be energized, means for energizing said electrodes in accordance with the operation of said detecting means, means for deriving a source of potential from a transmitted signal for powering the prosthesis, the potential of said source decreasing gradually following cessation of said transmitted signal and increasing gradually following resumption of said transmitted signal, means for shorting together all of said electrodes, means for detecting when the potential of said source is below a predetermined value, and means responsive to operation of said potential detecting means operating said shorting means while the potential of said source is still high enough to power the prosthesis.

96. An implantable tissue-stimulating prosthesis in accordance with claim 95 wherein said electrodes are associated with respective stimulation sites and said energizing means stimulates at most one stimulation site at any instant of time.

97. An implantable tissue-stimulating prosthesis in accordance with claim 96 wherein said energizing means includes a counter the states of which represent respective stimulation sites, means under control of said detecting means for advancing said counter in accordance with successive stimulation sites represented in a transmitted signal, and means for resetting said counter responsive to operation of said potential detecting means.

98. An implantable tissue-stimulating prosthesis in accordance with claim 97 wherein said detecting means includes control means for ascertaining the intensity of stimulation required at each stimulation site, and further including auxiliary means responsive to said control means ascertaining an intensity which exceeds a predetermined intensity for resetting said counter.

99. An implantable tissue-stimulating prosthesis in accordance with claim 98 further including means for preventing the operation of said auxiliary resetting means if said counter is already reset.

100. An implantable tissue-stimulating prosthesis in accordance with claim 99 wherein said transmitted signal consists of a pulse-modulated carrier whose pulse envelope represents sequential stimulation sites and the required stimulation intensities therefor.

101. An implantable tissue-stimulating prosthesis in accordance with claim 100 wherein the widths of pulses in said pulse envelope represent stimulation intensities.

102. An implantable tissue-stimulating prosthesis in accordance with claim 101 wherein said transmitted signal is transmitted in the form of sequential frames, and the position of each pulse in the pulse envelope of any frame represents the stimulation site to be stimulated.

103. An implantable tissue-stimulating prosthesis in accordance with claim 95 wherein said energizing means includes a counter the states of which represent respective stimulation sites, means under control of said detecting means for advancing said counter in accordance with successive stimulation sites represented in a transmitted signal, and means for resetting said counter responsive to operation of said potential detecting means.

104. An implantable tissue-stimulating prosthesis in accordance with claim 103 wherein said detecting means includes control means for ascertaining the intensity of stimulation required at each stimulation site, and further including auxiliary means responsive to said control means ascertaining an intensity which exceeds a predetermined intensity for resetting said counter.

105. An implantable tissue-stimulating prosthesis in accordance with claim 104 further including means for preventing the operation of said auxiliary resetting means if said counter is already reset.

106. An implantable tissue-stimulating prosthesis in accordance with claim 95 wherein said transmitted signal consists of a pulse-modified carrier whose pulse envelope represents sequential stimulation sites and the required stimulation intensities therefor.

107. An implantable tissue-stimulating prosthesis in accordance with claim 106 wherein the widths of pulses in said pulse envelope represent stimulation intensities.

108. An implantable tissue-stimulating prosthesis in accordance with claim 107 wherein said transmitted signal is transmitted in the form of sequential frames, and the position of each pulse in the pulse envelope of any frame represents the stimulation site to be stimulated.

109. An implantable tissue-stimulating prosthesis in accordance with claim 95 further including means for operating said shorting means in the absence of said detecting means detecting that any of said electrodes are to be energized.

110. An implantable tissue-stimulating prosthesis comprising a plurality of electrodes, means for detecting a transmitted signal which represents the manner in which said electrodes are to be energized, counter means whose states represent respective stimulation sites, means for advancing said counter means in accordance with successive stimulation sites represented in a transmitted signal, means for energizing said electrodes in accordance with the state of said counter means and the operation of said detecting means, means for deriving a source of potential from a transmitted signal for powering the prosthesis, the potential of said source decreasing gradually following cessation of said transmitted signal and increasing gradually following resumption of said transmitted signal, means for detecting when the potential of said source is below a predetermined value, and means responsive to operation of said potential detecting means for resetting said counter means while the potential of said source is still high enough to power the prosthesis.

111. An implantable tissue-stimulating prosthesis in accordance with claim 110 wherein said electrodes are associated with respective stimulation sites and said energizing means stimulates at most one stimulation site at any instant of time.

112. An implantable tissue-stimulating prosthesis in accordance with claim 142 wherein said detecting means includes control means for ascertaining the intensity of stimulation required at each stimulation site, and further including auxiliary means responsive to said control means ascertaining an intensity which exceeds a predetermined intensity for resetting said counter.

113. An implantable tissue-stimulating prosthesis in accordance with claim 112 further including means for preventing the operation of said auxiliary resetting means if said counter is already reset.

114. An implantable tissue-stimulating prosthesis in accordance with claim 114 wherein said transmitted signal consists of a pulse-modulated carrier whose pulse envelope represents sequential stimulation sites and the required stimulation intensities therefor.

115. An implantable tissue-stimulating prosthesis in accordance with claim 114 wherein the widths of pulses in said pulse envelope represent stimulation intensities.

116. An implantable tissue-stimulating prosthesis in accordance with claim 115 wherein said transmitted signal is transmitted in the form of sequential frames, and the position of each pulse in the pulse envelope of any frame represents the stimulation site to be stimulated.

117. An implantable tissue-stimulating prosthesis in accordance with claim 110 wherein said detecting means includes control means for ascertaining the intensity of stimulation required at each stimulation site, and further including auxiliary means responsive to said control means ascertaining an intensity which exceeds a predetermined intensity for resetting said counter means.

118. An implantable tissue-stimulating prosthesis in accordance with claim 117 further including means for preventing the operation of said auxiliary resetting means if said counter means is already reset.

119. An implantable tissue-stimulating prosthesis in accordance with claim 110 wherein said transmitted signal consists of a pulse-modulated carrier whose pulse envelope represents sequential stimulation sites and the required stimulation intensities therefor.

120. An implantation tissue-stimulating prosthesis in accordance with claim 119 wherein said transmitted signal is transmitted in the form of sequential frames, and the position of each pulse in the pulse envelope of any frame represents the stimulation site to be stimulated.

121. An implantable tissue-stimulating prosthesis in accordance with claim 110 wherein said transmitted signal is transmitted in the form of sequential frames, and the position of each pulse in the pulse envelope of any frame represents the stimulation site to be stimulated.

122. An implantable tissue-stimulating prosthesis comprising a plurality of electrodes, means for detecting a transmitted signal which represents the manner in which said electrodes are to be energized, capacitor means, means for deriving a source of potential across said capacitor means from a transmitted signal for powering the prosthesis, means for selectively energizing said electrodes from said potential source in accordance with the operation of said detecting means, means for detecting when the potential across said capacitor means falls below a predetermined value, means responsive to operation to said potential detecting means while the potential of said source is still high enough to power the prosthesis for placing the prosthesis in a predetermined system state, impedance means, and means responsive to said energizing means energizing none of said electrodes for connecting said impedance means across said capacitor means for controlling the discharge of said capacitor means at a predetermined rate.

123. An implantable tissue-stimulating prosthesis in accordance with claim 122 wherein said energizing means includes a counter the states of which represent respective stimulation sites, and means under control of said detecting means for advancing said counter in accordance with successive stimulation sites represented in a transmitted signal, and wherein said predetermined system state is a state in which said counter is reset.

124. An implantable tissue-stimulating prosthesis in accordance with claim 123 wherein said detecting means includes control means for ascertaining the intensity of stimulation required at each stimulation site, and further including means responsive to said control means ascertaining an intensity which exceeds a predetermined intensity for resetting said counter.

125. An implantable tissue-stimulating prosthesis in accordance with claim 124 further including means for preventing the operation of said resetting means if said counter is already reset.

126. An implantable tissue-stimulating prosthesis in accordance with claim 123 further including means responsive to the prosthesis being placed in said predetermined system state for shorting together all of said electrodes.

127. A cochlear prosthesis comprising a plurality of electrodes, pairs of which are associated with respective stimulation sites and with at least almost all of said electrodes being included in each of at least two different pairs, means for detecting a transmitted information signal which represents both stimulation sites and stimulation intensities required therefor, means under control of said detecting means for energizing the pair of electrodes associated with a represented stimulation site with successive opposite-polarity current pulses in accordance with the respective represented stimulation intensity, said information signal representing a stimulation intensity in the form of a pulse width and said information signal being formatted in successive frames with each frame including a plurality of pulses in a predetermined sequence corresponding to respective stimulation sites, said energizing means being capable of energizing successive pairs of electrodes in a predetermined sequence corresponding to the predetermined pulse sequence in each frame, means for shorting together all of said electrodes, means for detecting a pulse width in said information signal which exceeds a predetermined width, and means responsive to operation of said pulse width detecting means for operating said shorting means.

128. A cochlear prosthesis in accordance with claim 127 wherein a stimulation site is represented in an information signal frame by a respective pair of pulses, and said energizing means controls the intensity of each of the opposite-polarity current pulse applied to a represented stimulation site in accordance with the width of a different one of the respective pair of pulses.

129. A cochlear prosthesis comprising a plurality of electrodes, pairs of which are associated with respective stimulation sites and with at least almost all of said electrodes being included in each of at least two different pairs, means for detecting a transmitted information signal which represents both stimulation sites and stimulation intensities required therefor, means under control of said detecting means for energizing the pair of electrodes associated with a represented stimulation site with successive opposite-polarity current pulses in accordance with the respective represented stimulation intensity, means for shorting together all of said electrodes, and means for operating said shorting means in the absence of said detecting means detecting an information signal which represents a requirement for site stimulation.

130. A cochlear prosthesis comprising a plurality of electrodes, pairs of which are associated with respective stimulation sites and with at least almost all of said electrodes being included in each of at least two different pairs, means for detecting a transmitted information signal which represents both stimulation sites and stimulation intensities required therefor, means under control of said detecting means for energizing the pair of electrodes associated with a represented stimulation site with successive opposite-polarity current pulses in accordance with the respective represented stimulation intensity, means for shorting together all of said electrodes, means for detecting a represented stimulation intensity in said information signal which exceeds a predetermined intensity, and means responsive to operation of said stimulation intensity detecting means for operating said shorting means.

131. A cochlear prosthesis comprising a plurality of electrodes, pairs of which are associated with respective stimulation sites and with at least almost all of said electrodes being included in each of at least two different pairs, means for detecting a transmitting information signal which represents both stimulation sites and stimulation intensities required therefor, means under control of said detecting means for energizing the pair of electrodes associated with a represented stimulation site with successive opposite-polarity current pulses in accordance with the respective represented stimulation intensity, means for deriving a source of power for said detecting and energizing means from the detected information signal, means for shorting together all of said electrodes, means for detectng a predetermined drop in the level of said source of power, and means responsive to said level drop detecting means for operating said shorting means.

132. A cochlear prosthesis comprising a plurality of electrodes, pairs of which are associated with respective stimulation sites and with at least almost all of said electrodes being included in each of at least two different pairs, means for detecting a transmitted information signal which represents both stimulation sites and stimulation intensities required therefor, means under control of said detecting means for energizing the pair of electrodes associated with a represented stimulation site with successive opposite-polarity current pulses in accordance with the respective represented stimulation intensity, means for inhibiting the energizations of all of said electrodes, means for determining if the detected information signal is inconsistent with a predetermined format, and means responsive to operation of said determining means for operating said inhibiting means.

133. A cochlear prosthesis in accordance with claim 132 wherein said inhibiting means is further operative to short together all of said electrodes.

134. A cochlear prosthesis in accordance with claim 132 further including means for re-synchronizing the operation of said energizing means to said information signal, and means responsive to said determining means for controlling operation of said re-synchronizing means.

135. A cochlear prosthesis comprising a plurality of electrodes associated with each other in pairs, means for detecting a transmitted information signal, said information signal being in the form of sequential frames each of which identifies required stimulation intensities for respective paired electrodes in a predetermined sequence, means responsive to said detecting means for selecting and energizing at most a single electrode pair at any instant but for selecting all of the electrode pairs and energizing them with the required respective stimulation intensities in the same sequence in which the electrode pairs are identified in a frame of said information signal, means for deriving a source of power for said detecting means and said selecting and energizing means from the transmitted information signal, means for shorting together all of said electrodes, means for detecting a predetermined drop in the level of said source of power, and means responsive to said level drop detecting means for operating said shorting means.

136. A cochlear prosthesis comprising a plurality of electrodes associated with each other in pairs, means for detecting a transmitted information signal, said information signal being in the form of sequential frames each of which identifies required stimulation intensities for respective paired electrodes in a predetermined sequence, means responsive to said detecting means for selecting and energizing at most a single electrode pair at any instant but for selecting all of the electrode pairs and energizing them with the required respective stimulation intensities in the same sequence in which the electrode pairs are identified in a frame of said information signal, means for inhibiting the energizations of all of said electrodes, means for determining if the detected information signal is inconsistent with a predetermined format, and means responsive to operation of said determining means for controlling operation of said inhibiting means.

137. A cochlear prosthesis in accordance with claim 136 wherein said inhibiting means is further operative to short together all of said electrodes.

138. A cochlear prosthesis in accordance with claim 136 further including means for re-synchronizing the operation of said selecting and energizing means to sequential information signal frames, and means responsive to operation of said determining means for controlling operation of said re-synchronizing means.

139. A cochlear prosthesis comprising a plurality of electrodes associated with each other in pairs; means for detecting a transmitted information signal, said information signal being in the form of sequential frames each of which identifies required stimulation intensities for respective paired electrodes in a predetermined sequence; means responsive to said detecting means for selecting and energizing at most a single electrode pair at any instant but for selecting all of the electrode pairs and energizing them with the required respective stimulation intensities in the same sequence in which the electrode pairs are identified in a frame of said information signal, said selecting and energizing means including a counter which is advanced by detected frame information and whose count selects a respective electrode pair, said counter including a reset state; and means responsive to said counter being reset for shorting together all of said electrodes.

140. A cochlear prosthesis in accordance with claim 139 further including means responsive to the detection of the end of a frame for resetting said counter.

141. A cochlear prosthesis in accordance with claim 139 further including means responsive to the detection of the start of a frame for resetting said counter.

142. A cochlear prosthesis in accordance with claim 139 further including means responsive to the detection in a frame of said information signal of any required stimulation intensity which exceeds a predetermined intensity for resetting said counter.

143. A cochlear prosthesis comprising a plurality of electrodes associated with each other in pairs, means for detecting a transmitted information signal, said information signal being in the form of sequential frames each of which identifies required stimulation intensities for respective paired electrodes in a predetermined sequence, means responsive to said detecting means for selecting and energizing at most a single electrode pair at any instant but for selecting all of the electrode pairs and energizing them with the required respective stimulation intensities in the same sequence in which the electrode pairs are identified in a frame of said information signal, said selecting and energizing means including a counter which is advanced by detected frame information and whose count selects a respective electrode pair, and means responsive to the detection of the end of a frame for resetting said counter.

144. A cochlear prosthesis comprising a plurality of electrodes associated with each other in pairs, means for detecting a transmitted information signal, said information signal being in the form of sequential frames each of which identifies required stimulation intensities for respective paired electrodes in a predetermined sequence, means responsive to said detecting means for selecting and energizing at most a single electrode pair at any instant but for selecting all of the electrode pairs and energizing them with the required respective stimulation intensities in the same sequence in which the electrode pairs are identified in a frame of said information signal, said selecting and energizing means including a counter which is advanced by detected frame information and whose count selects a respective electrode pair, and means responsive to the detection of the start of a frame for resetting said counter.

145. A cochlear prosthesis comprising a plurality of electrodes associated with each other in pairs, means for detecting a transmitted information signal, said information signal being in the form of sequential frames each of which identifies required stimulation intensities for respective paired electrodes in a predetermined sequence, means responsive to said detecting means for selecting and energizing at most a single electrode pair at any instant but for selecting all of the electrode pairs and energizing them with the required respective stimulation intensities in the same sequence in which the electrode pairs are identified in a frame of said information signal, said selecting and energizing means including a counter which is advanced by detected frame information and whose count selects a respective electrode pair, and means responsive to the detection in a frame of said information signal of any required stimulation intensity which exceeds a predetermined intensity for resetting said counter.

* * * * *